United States Patent [19]
Zhang et al.

[11] Patent Number: 5,491,627
[45] Date of Patent: Feb. 13, 1996

[54] METHOD AND SYSTEM FOR THE DETECTION OF MICROCALCIFICATIONS IN DIGITAL MAMMOGRAMS

[75] Inventors: Wei Zhang, Chicago; Kunio Doi, Willowbrook, both of Ill.

[73] Assignee: Arch Development Corporation, Chicago, Ill.

[21] Appl. No.: 60,531

[22] Filed: May 13, 1993

[51] Int. Cl.⁶ ................................ A61B 6/00
[52] U.S. Cl. ........................ 364/413.2; 128/664
[58] Field of Search ............... 364/413.13, 413.22; 382/2, 6, 19; 128/664

[56] References Cited

U.S. PATENT DOCUMENTS

| | | |
|---|---|---|
| 4,839,807 | 6/1989 | Doi et al. |
| 4,841,555 | 6/1989 | Doi et al. |
| 4,851,984 | 7/1989 | Doi et al. |
| 4,875,165 | 10/1989 | Fencil et al. |
| 4,907,156 | 3/1990 | Doi et al. |
| 4,918,534 | 4/1990 | Lam et al. |
| 5,072,384 | 12/1991 | Doi et al. |
| 5,133,020 | 7/1992 | Giger et al. |
| 5,150,292 | 9/1992 | Hoffmann et al. |
| 5,224,177 | 6/1993 | Doi et al. |

OTHER PUBLICATIONS

Robert M. Nishikawa et al., "Computer–Aided Detection of Clustered Microcalcifications On Digital Mammograms", Submitted to Med. & Biological Engineering & Computing, Apr. 9, 1992.
Zhang et al., "Parallel Distributed Processing Model with Local Space–invariant Interconnections and its Opticals Architecture" Appl. Opt. 29, 4790–7 (1990).
Zhang et al., "Image Processing of Human Corneal Endothelium Based on a Learning Network", Appl. Opt. 30, 4211–7 (1991).
Zhang et al., "Error Back Propagation with Minimum–entropy Weights: A technique for Better Generalization of 2–D Shift–invariant NNS," Proc. Intl. Joint Conf. Neural Networks, Seatle 1991, I–212 through I–215.
"Automated Detection of Microcalcifications on Mammograms: New Feature–Extraction Techniques with Morphologic Filters," Robert M. Nishikawa, et al., 76th Scientific Assembly and Annual Meeting of RSNA, Radiology 177 (P), 288 (1990) (abstract).
"Application of Neural Networks to Mammographic Diagnosis of Breast Cancer," Yuzheng Wu, et al., 76th Scientific Assembly and Annual Meeting of RSNA, Radiology 177 (P), 149 (1990) (abstract).
"Computerized Detection of Clustered Microcalcifications in Digital Mammograms: Applications of Artificial Neural Networks," Yuzheng Wu, et al., Med. Phys. 19 (3), May/Jun. 1992, pp. 555–560.

(List continued on next page.)

*Primary Examiner*—Jack B. Harvey
*Assistant Examiner*—Xuong M. Chung-Trans
*Attorney, Agent, or Firm*—Oblon, Spivak, McClelland, Maier & Neustadt

[57] ABSTRACT

A method and system for the detection of microcalcifications in digital mammograms. Digital mammograms are obtained and regions-of-interest (ROIs) are selected therefrom which contain suspected microcalcifications, either individual or clustered microcalcifications. The suspect ROIs are background-trend corrected, followed by Fourier transformation and power spectrum calculation to perform detection in the frequency domain. Detection can also be carried out in the spatial domain by omitting the Fourier transformation and power spectrum calculation. The ROI is then scaled for input into a neural network trained to detect microcalcifications. The neural network outputs ROIs with detected microcalcifications. The method and system can also include normalizing the background-trend corrected ROIs and imputing the normalized ROI to a shift-invariant neural network trained to detect microcalcifications. The output ROI of the shift-invariant neural network is thresholded to remove additional false positive detections, and then the thresholded ROI undergoes a cluster detection to detect clustered microcalcifications. Feature extraction techniques can be applied to the remaining ROI to remove additional false positive detections.

48 Claims, 15 Drawing Sheets

OTHER PUBLICATIONS

"Improvement in Radiologists' Detection of Clustered Microcalcifications on Mammograms: The Potential of Computer–Aided Diagnosis," Heang–Ping Chan, et al., INVESTIGATIVE RADIOLOGY, vol. 25, No. 10, Oct. 1990, pp. 1102–1110.

"Image Feature Analysis and Computer–Aided Diagnosis in Digital Radiography: Detection and Characterization of Interstitial Lung Disease in Digital Chest Radiographs," Sigehiko Katsuragawa, et al., Med. Phys. 15 (3), May/Jun. 1988, pp. 311–319.

$w(i,j: x,y)=w(i-x,j-y)$

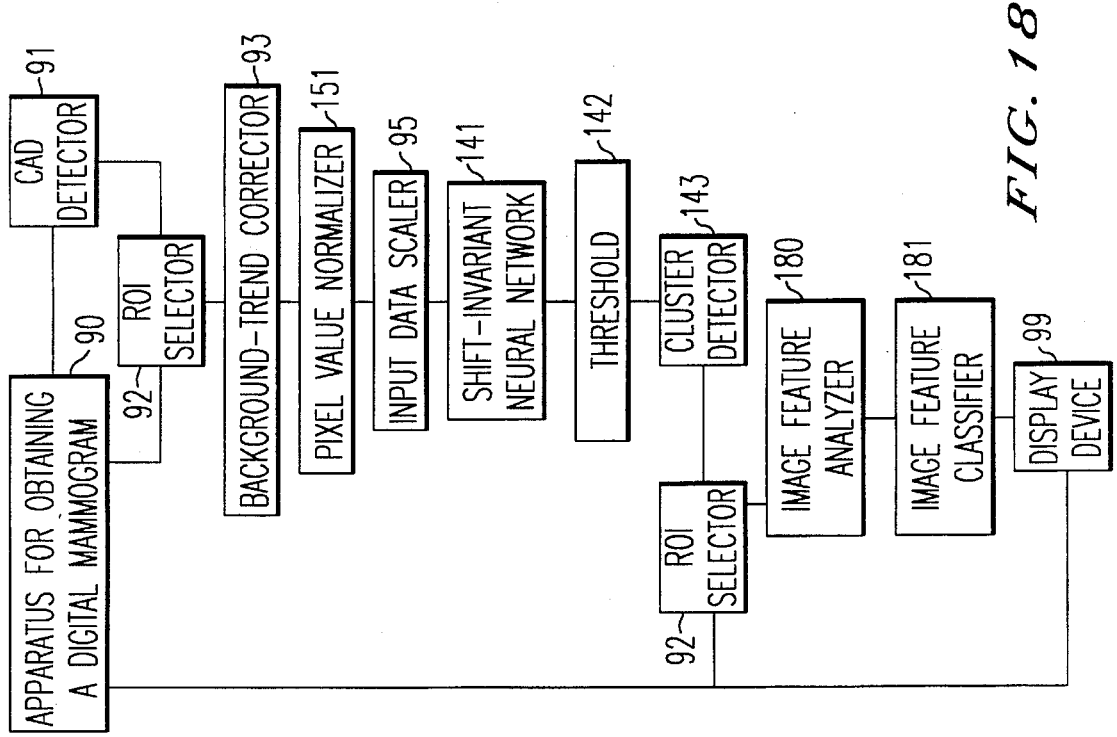

METHOD AND SYSTEM FOR THE DETECTION OF MICROCALCIFICATIONS IN DIGITAL MAMMOGRAMS

The present invention was made in part with U.S. Government support under NIH grants/contracts CA24806 and CA47043. The U.S. Government has certain rights in the invention.

BACKGROUND OF THE INVENTION

1. Field of the Invention

The present invention relates to a method and system for the detection of microcalcifications in digital mammograms, and in particular to a method and system for the detection of clustered microcalcifications in digital mammograms using a shift-invariant neural network.

2. Discussion of the Background

Breast cancer causes 44,000 deaths per year in the United States. Mammography has been proven to be the primary diagnostic procedure for the early detection of breast cancer. Between 30% and 50% of breast carcinomas demonstrate microcalcifications upon histologic examination. Therefore, clustered microcalcifications in mammograms are an important sign in the detection of breast carcinoma. To assist radiologists in detecting clustered microcalcifications on mammograms, an automated computerized scheme based on filtering and feature extracting techniques has been developed as reported in Chan et al., "Improvement in Radiologist's Detection of Clustered Microcalcifications on Mammograms: The Potential of Computer-aided Diagnosis," Invest Radiol 25, 1102–10 (1990). The automated computer scheme identifies a small region of potential clustered microcalcifications, which is then indicated on the digitized mammogram. In an analysis of 78 mammograms, 85% of the clusters were detected with 1.5 false positive detections per image, which do not actually contain clustered microcalcifications.

It is generally desirable to improve the sensitivity of the computer-automated detection (CAD) scheme in order to detect the most subtle cases. However, as the sensitivity increases with this CAD scheme, the false-positive detection rate will also increase. To improve the overall performance, an artificial neural network has been applied to eliminate some of the false-positive detections indicated by the CAD scheme (see Wu et al., "Computerized Detection of Clustered Microcalcifications in Digital Mammograms: Applications of Neural Networks," Med. Phys. 19, 555–60 (1992). The neural network used in this study was a conventional three layer feed-forward neural network with a single output unit. The power spectra of the regions of interest (ROIs) indicated by the CAD scheme were used as the input of the neural network. The neural network was trained to classify positive or negative ROIs with its output value of 1 or 0, respectively. In the study discussed above, about 20% of the false-positive detections could be eliminated by the neural network without any loss of the positive detections.

Artificial neural networks have been shown to be a powerful tool for pattern recognition and data classification. The major difference between neural networks and conventional algorithmic approaches to information processing is that the problems are not solved by use of a predetermined algorithm, but rather by "training" using examples repeatedly. Therefore, the issue of generalization, whether training a neural network so that it would respond reasonably well to inputs not present in the training database, is very important (see, for example, Zhang et al. "Error Back Propagation with Minimum-entropy Weights: A Technique for Better Generalization of 2-D Shift-invariant NNs," Proc. Intl. Joint Conf. Neural Networks," Seattle 1991, I-212 through I-215). Without proper generalization, the potential advantage of neural networks will be limited, because one could simply use a look-up table to solve the problem. A neural network with high generalizing ability implies that one can obtain the high performance by training with a few training examples, as compared to that by a neural network with low generalizing ability. This is very important for application of neural networks to medical image processing and decision making, because usually the databases in medical applications are very large and the training of neural networks can be very time consuming.

SUMMARY OF THE INVENTION

It is therefore an object of the present invention to provide a novel method and system for the detection of clustered microcalcifications in digital mammograms.

A second object of the present invention is to provide a novel method and system for the detection of clustered microcalcifications in digital mammograms using a shift-invariant neural network.

Another object of the present invention is to reduce the number of false positive detections while preserving all true positive detections.

A further object of the invention is to perform clustered microcalcification detection in a digital mammogram using regions of interest in the spatial domain.

A still further object of the present invention is to perform clustered microcalcification detection in a digital mammogram independent of the relative locations of each microcalcification and the orientation of the cluster.

Still another object of the present invention is to detect clustered microcalcifications in a digital mammogram using both a shift-invariant neural network and feature extraction techniques.

Another object of the present invention is to use feature thresholding to remove false-positives in addition to those removed by processing of the shift-invariant neural network.

Accordingly, these and other objects are obtained by a method according to a first embodiment of the invention of detecting microcalcifications in digital mammograms including the steps of obtaining a digital mammogram, extracting regions of interest from the mammogram suspected of containing a microcalcification, converting the regions of interest into numerical data, inputting the numerical data into a neural network trained to detect microcalcifications for processing of the numerical data, the neural network outputting corresponding output images, and detecting a microcalcification in the digital mammogram using the output images.

The method according to the first embodiment may also include background-trend correcting the regions of interest to produce regions of interest having a uniform background-trend, Fourier transforming the background-trend corrected regions of interest, calculating power spectra from the Fourier-transforms, and converting the power spectra into the numerical data.

The system according to the first embodiment for detecting microcalcifications in a digital mammogram includes a device for obtaining a digital mammogram, a detector connected to this device to detect suspected microcalcifications in the digital mammogram, a region of interest selector for selecting regions of interest in the digital mammogram corresponding to the suspected microcalcifications, a region of interest processing device, an input data scaler for scaling the processed region of interest, a neural network which receives the numerically scaled regions of interest and outputs corresponding output images, and a microcalcification detector for detecting microcalcifications in the output images.

The region of interest processing device may include a background-trend corrector for correcting the background of the selected regions of interest, a Fourier transformer for Fourier transforming the background-trend corrected regions of interest, and a power spectrum calculator for calculating corresponding power spectra.

These and other objects are also obtained by a method according to a second embodiment of detecting clustered microcalcification in digital mammograms using a shift-invariant neural network including the steps of obtaining a digital mammogram, extracting regions of interest from the digital mammogram suspected of containing a clustered microcalcification, converting the regions of interest into numerical data, and inputting the numerical data into a shift-invariant neural network trained to detect clustered microcalcifications, processing the numerical data using the shift-invariant neural network to produce output images, and detecting a clustered microcalcification in the digital mammogram using the output images.

The shift-invariant neural network can be trained using a modified error back propagation method to detect all of the true microcalcifications while eliminating false-positive microcalcification detections.

The system according to the second embodiment includes a device for obtaining a digital mammogram, a detector for detecting suspected microcalcifications in the digital mammogram, a region of interest selector for selecting regions of interest in the digital mammogram corresponding to the suspected microcalcifications, a region of interest processing device for producing a processed region of interest, an input data scaler for numerically scaling the processed regions of interest, a shift-invariant neural network trained to detect clustered microcalcifications receiving the numerically scaled regions of interest, and a microcalcification detector for detecting microcalcifications using the output of the shift-invariant neural network.

The method according to the second embodiment may be modified to a third embodiment which further includes a step of feature extraction of the microcalcifications detected by the shift-invariant neural network and microcalcification detector. By performing feature extraction, additional false-positive microcalcification detections can be removed while maintaining all of the true detected microcalcifications. The feature extraction may include feature thresholding using empirically derived thresholds.

The third embodiment of the system according to the invention includes, in addition to that of the second embodiment, an image feature extraction device for performing feature extraction on suspected microcalcifications in the digital mammogram detected by the neural network. Using both the neural network and the feature extraction device, a large number of false-positive microcalcification detections can be removed.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 18 is a block diagram of the system according to a third embodiment of the invention; and FIG. 19 is a block diagram of a prior art computer-aided diagnostic apparatus.

DESCRIPTION OF THE PREFERRED EMBODIMENTS

Figure 1:
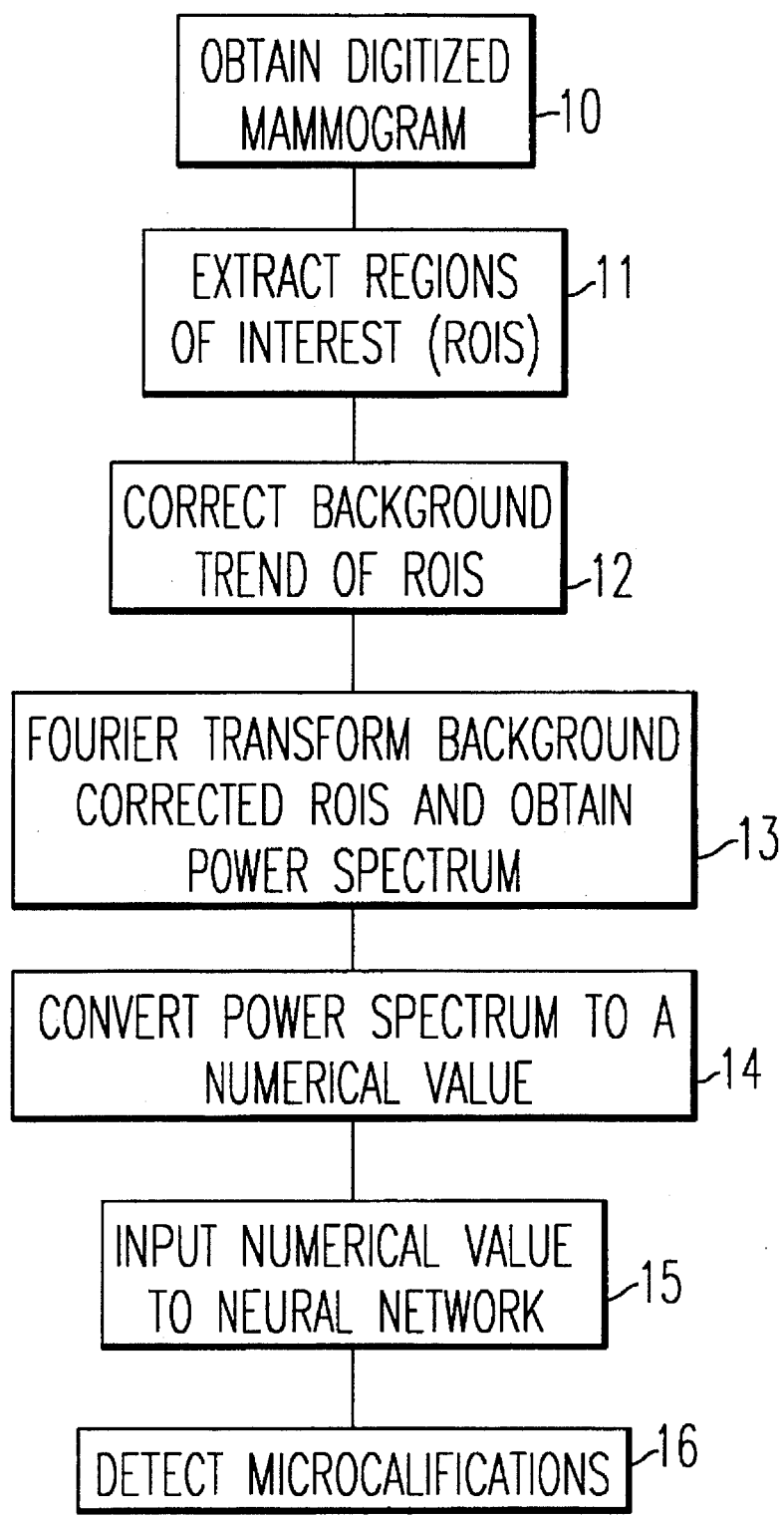
FIG. 1 is a flow chart of a method according to a first embodiment of the invention.

Referring to the drawings, and in particular to FIG. 1, a first embodiment of the method according to the invention will be described. First, as indicated in step 10 of FIG. 1, mammograms are taken using conventional techniques, such as x-ray, and then digitized. This may be carried out, for example, by digitizing a conventional screen film image on a drum scanner system with a selected pixel size, such as $0.1 \times 0.1$ mm$^2$. Regions of interest (ROIs) are then extracted from the digitized mammograms as described in U.S. Pat.

No. 4,907,156 to Doi et al., the disclosure of which is incorporated herein by reference, that contain a number of microcalcifications (step 11). ROIs can also be selected which contain clustered microcalcifications. The selection is performed using a computer-aided diagnosis routine generally as shown in FIG. 18 and described in more detail in U.S. Pat. No. 4,907,156.

FIG. 18 includes a device for obtaining digital mammograms 90, as described above, which inputs the digital mammogram to a computer-aided diagnosis (CAD) device 191. The device 191 includes a device for producing a signal-enhanced image 192 and a device for producing a signal-suppressed image 193. The signal-enhanced and signal-suppressed images are input to an image differencer 184 which produces an image being the difference between the signal-enhanced and signal-suppressed images. The difference image is output by device 194 to feature extraction device 195 which produces ROIs containing suspect microcalcifications.

Different ROIs contain different background levels that are not uniform. To isolate the microcalcifications from the nonuniform background, a background-trend correction technique is applied to the ROI (step 12). For example, a two-dimensional polynomial curve fitting (to the third degree) can be used to fit a background surface of the ROI (see U.S. Pat. No. 4,851,984 to Doi et al.). The fitted background surface is then subtracted from the original ROI to produce a background-trend corrected ROI. After the background-trend correction, all selected ROIs will have the same background level and approximately the same mean pixel value.

Figure 2:
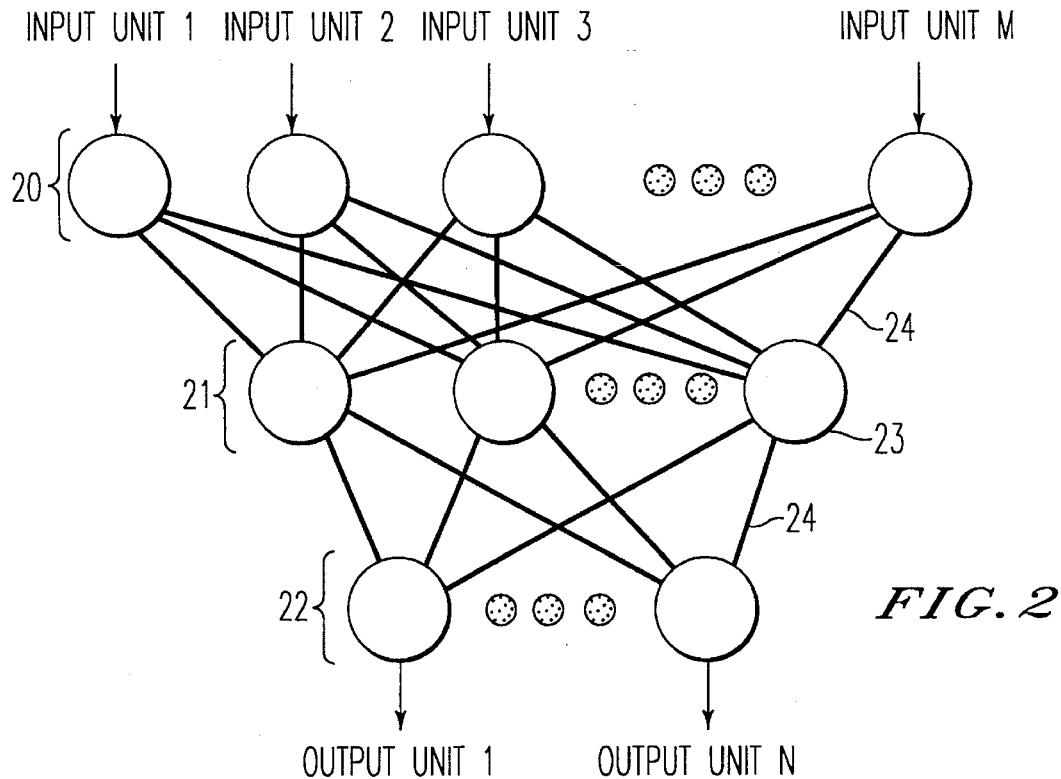
FIG. 2 is a diagram of a neural network of the first embodiment of the invention.

The microcalcifications also have different relative positions from one ROI to another. These relative differences should be corrected to improve detection results. A Fourier transformation could be applied to the ROIs which would "centralize" the microcalcifications in the spatial frequency domain. Power spectra can be calculated from the Fourier transforms of the ROIs, as indicated in step 13. Since the power spectra are independent of the relative locations of the microcalcifications in the ROI, the microcalcifications can be classified based on their spatial frequency patterns, as shown in FIG. 2. As the power spectra are symmetric about the origin, only one half of the spectra is needed.

The power spectra are then converted using a logarithmic scale to reduce the dynamic range of the data, and then the resulting logarithm is scaled to a numerical value, typically between 1 and 0 (step 14). These values are input to a feed-forward neural network (step 15). The neural network outputs ROIs with detected microcalcifications which can be displayed on the original mammogram (step 16), as described below.

The neural network configuration is selected to optimize the detection results, and is shown in FIG. 2. The neural network of FIG. 2 is a three-layer, feed-forward neural network. The network contains an input layer 20 having input units 1, 2, ... M, one hidden layer 21 having hidden units 23, and an output layer 22 having output units 1, ... N. The layers are connected via weighted links 24. Although one particular neural network configuration is illustrated, other configurations are possible within the scope of the invention.

A back-propagation algorithm with generalized delta rule was used to train the neural network, and a nonlinear logistic function was used as the activation function for each processing unit in the neural network, such as $$O_{pj} = \frac{1}{1 + \exp\left(\sum_i w_{ji} \times O_{pi} + \theta_j\right)}$$

where $o_{pj}$ is the jth element of the actual output pattern produced by the presentation of input pattern p, $w_{ji}$ is the weight from the ith to the jth units and $\Theta_j$ is the threshold of the jth units. In the training process, the internal parameters of the connections between layers (including threshold values of each unit) are adjusted iteratively so that the difference between the output values and the desired results is minimized. This can be accomplished by the following rule:

$$\Delta w_{ji}(n+1) = \eta(\delta_{pj} o_{pi}) + \alpha \Delta w_{ji}(n)$$

where n indexes the number of iterations, $\eta$ is the learning rate, $\delta_{pj}$ is the error signal, which is related to the difference between the output of the neural network and the target (desired) output, and $\alpha$ is a momentum term that determines the effect of past weight changes on the current direction of movement in weight space. This back propagation technique is described in "Parallel Distributed Processing" by D. E. Rumelhart and J. L. McClellend, editors, (MIT, Cambridge, Mass. 1986), pp. 318–362. In the testing process, the trained neural network maps the input patterns to corresponding output values, utilizing the internal parameters established in the training. The output values are analyzed by comparison with the desired results.

In this example, the number of input units of the network is selected based on the number of pixels in half of the power spectrum in the frequency domain and the number of pixels in a ROI in the spatial domain. Thus, only half of the power spectra are input to the neural network. The number of hidden units was selected empirically such that the difference between the outputs of the neural network and the desired outputs were minimized, using the receiver operating characteristic (ROC) approach. One output unit was used, and the momentum $\eta$ and learning rate $\alpha$ as defined above were selected to be 0.9 and 0.1, respectively. The following table shows typical parameters of the neural network according to the first embodiment of the invention. It should be noted that other parameters are possible within the scope of the invention.

TABLE 1

| Domain | microcalc. type | input units | hidden units | output units | iterations |
|---|---|---|---|---|---|
| spatial | individual | 64 | 5 | 1 | >5000 |
|  | clustered | 1024 | 15 | 1 | 1000 |
| frequency | individual | 32 | 5 | 1 | 1000 |
|  | clustered | 512 | 15 | 1 | 1000 |

As an example of the first embodiment of the method according to the invention, individual microcalcifications from a total of 60 ROIs of 8×8 pixels from three digital mammograms were selected. Half the ROIs, each of which contained one single microcalcification, were defined as positive ROIs. The other half of the ROIs, which were selected visually and uniformly by trained radiologists from normal areas of the mammograms, contained no microcalcifications and were defined as negative ROIs.

Figure 3:
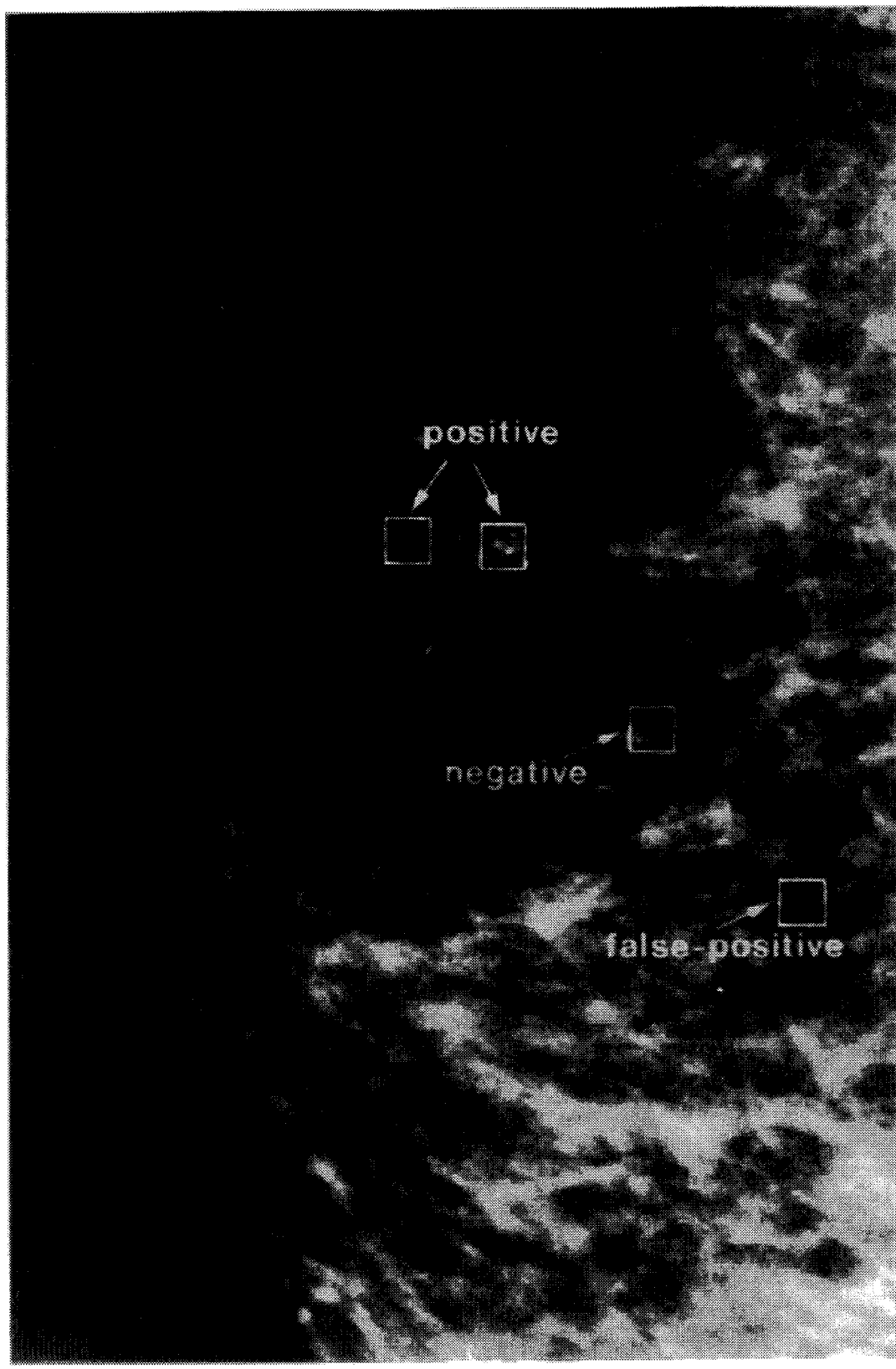
FIG. 3 is a mammogram with positive, false-positive and negative regions of interest (ROIs) indicated.

As a second example of the first embodiment of the method according to the invention, clustered microcalcifications in 168 ROIs selected from 34 digital mammograms were chosen. A larger ROI size is required, such as 32×32 pixels. The 168 ROIs included 56 positive ROIs that contained clustered microcalcifications, 56 negative ROIs selected visually and uniformly by trained radiologists from normal areas of the mammograms and contained no clustered microcalcifications, and 56 false positive ROIs were selected using the above described CAD scheme. FIG. 3 illustrates the selection of ROIs from a mammogram. This mammogram contains two positive ROIs containing clustered microcalcifications, one negative ROI, and one ROI containing a false positive cluster.

Figure 4:
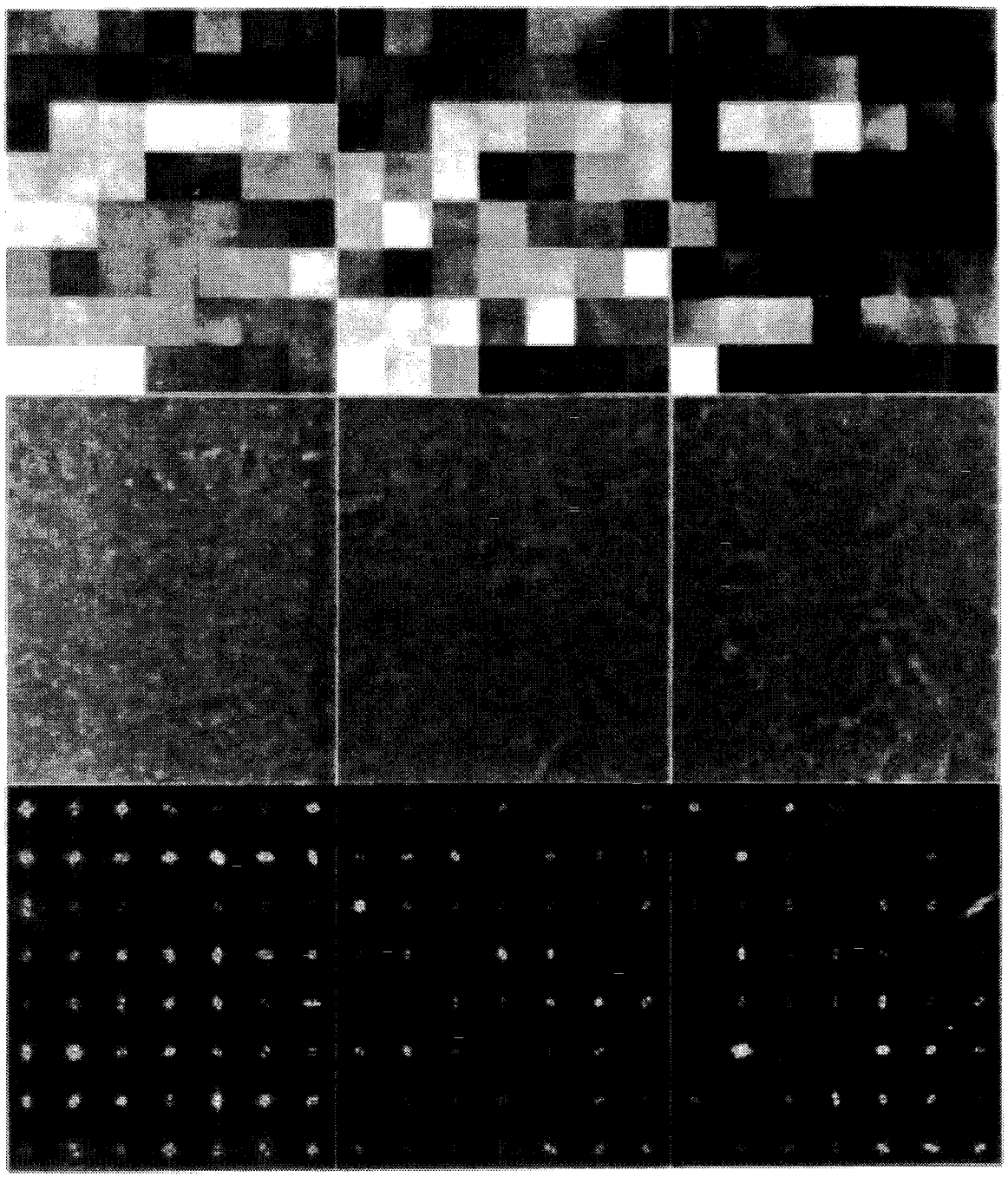
FIG. 4 is a diagram of the database of ROIs, background-trend corrected ROIs and power spectrum of the corrected ROIs.

FIG. 4 illustrates the database for the clustered microcalcifications, with the top row containing 56 ROIs of positive, negative, and false-positive clustered microcalcifications, moving left to right, the middle row containing the corresponding background-trend corrected ROIs, and the bottom row containing the power spectra of the corresponding background-trend corrected ROIs. Only half of the pixels of the power spectra are used as input, as the spectra are symmetric with respect to positive and negative frequencies.

The positive ROIs in FIG. 4 generally contain greater low-frequency components than do either negative or false-positive ROIs. The low-frequency components in the power spectra of clustered microcalcifications may be contributed largely by the relative positions between microcalcifications in a cluster and the finite sizes of the microcalcifications. To illustrate the difference quantitatively, the average power spectrum for each group of ROIs was calculated.

Figure 5:
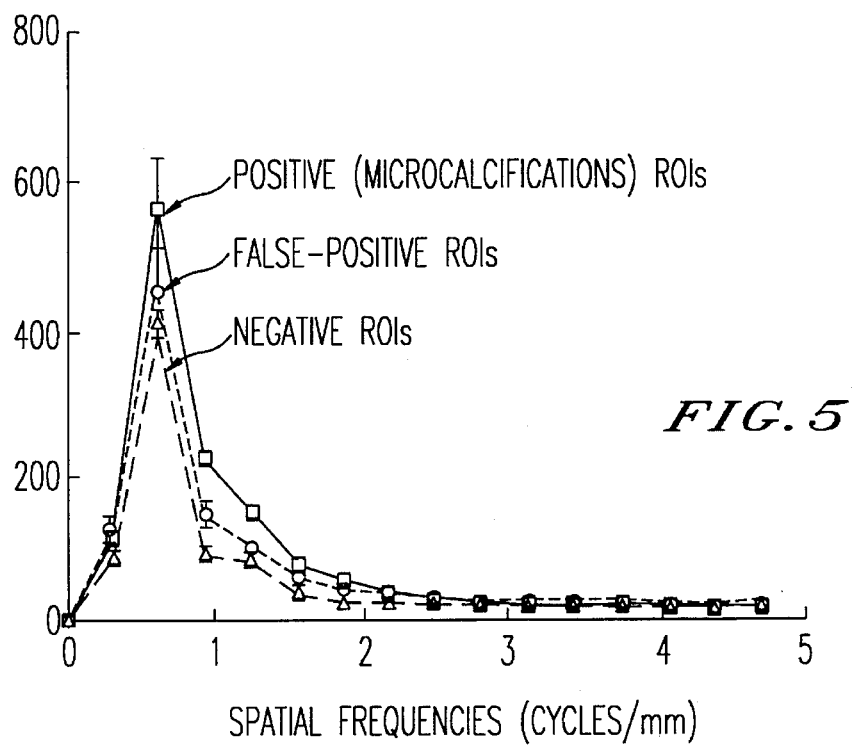
FIG. 5 is a graph of the power spectrum versus spatial frequency illustrating the detection of microcalcifications.

FIG. 5 shows the three averaged power spectra for positive, negative, and false-positive ROIs. It is evident that positive ROIs have greater low-frequency components, on average, than do negative ROIs. The averaged power spectrum for false-positive ROIs, which "look like" microcalcifications to the computerized detection scheme, was between the spectrum of positive and the spectrum of negative ROIs. However, the difference in the spectra among the three groups of ROIs was very small and therefore detection among the three is difficult.

In testing the neural network according to the first embodiment, detection of microcalcifications in the frequency domain was carried out. First, in order to test the capability of the neural networks according to the first embodiment to learn the mammographic patterns of microcalcifications, a consistency test was conducted. The neural networks were first trained with all the cases in the database and then tested with the same cases used in the training. The output values from the neural networks were compared with the desired results obtained from trained radiologists.

For individual and clustered microcalcifications, 60 and 168 cases, respectively, as described above, were used for training and testing. In both situations, the neural networks correctly distinguished all positive ROIs from negative and false-positive ROIs. This result of a 100% correct classification rate suggests that neural networks are capable of learning all of the input patterns used in this study. This is a significant improvement over the CAD scheme, which typically did not detect all of the positive ROIs.

The consistency test indicated that the networks were able to "remember" all of the patterns that were used for training. However, what is more important is whether a neural network can learn a generalized pattern from the examples provided and whether it can then make correct predictions/classifications for new cases that were not included in the training. Therefore, a "jack-knife" method was employed to test the network's generalizing ability. With the jack-knife method, one half of the cases were selected randomly from the database for training of the network, and then the other half of the cases were used for testing of the trained network. The output values were then compared with the desired values. Various combinations of training and testing pairs were selected by using a random number generator, and the results were analyzed by using receiver operating characteristic (ROC) analysis. ROC curves were obtained by fitting continuous output data from the neural networks using LABROC4 program developed by Metz et al ("New Methods for Estimating a Binormal ROC Curve from Continuously-distributed Test Results", presented at the 1990 Joint Meetings of the American Statistical Society and the Biometric Society, Anaheim, Calif., August 1990).

Figure 6:
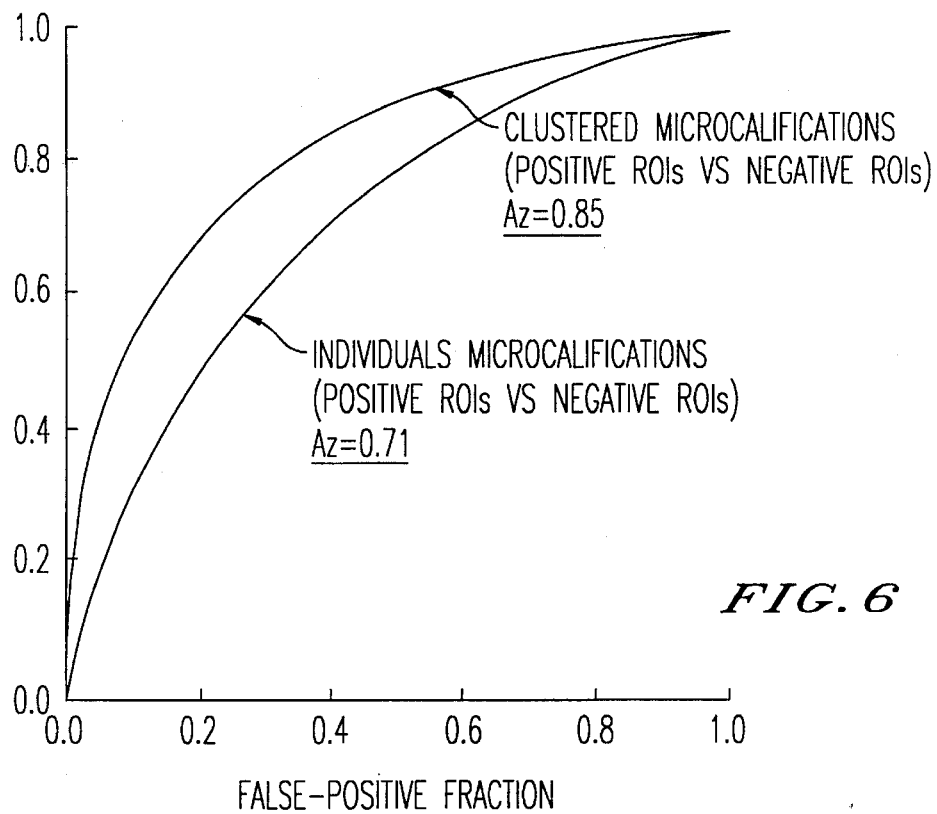
FIG. 6 is a graph comparing the detection of individual and clustered microcalcifications as a function of positive versus false-positive fraction using receiver operating characteristic (ROC) analysis.

FIG. 6 shows the ROC curves for distinguishing positive ROIs from negative ROIs for individual and clustered microcalcifications in the frequency domain. Twenty pairs of randomly selected training and testing combinations were used to generate the ROC curves. It is evident from FIG. 6 that, in the frequency domain, the network performs better in detecting clustered microcalcifications than in identifying individual microcalcifications. This result is probably due to the fact that the spatial patterns of isolated signal components such as microcalcifications are centered in the frequency domain by the shifting property of the Fourier transformation, and this centering effect is stronger for multiple microcalcifications than a single microcalcification.

Figure 7:
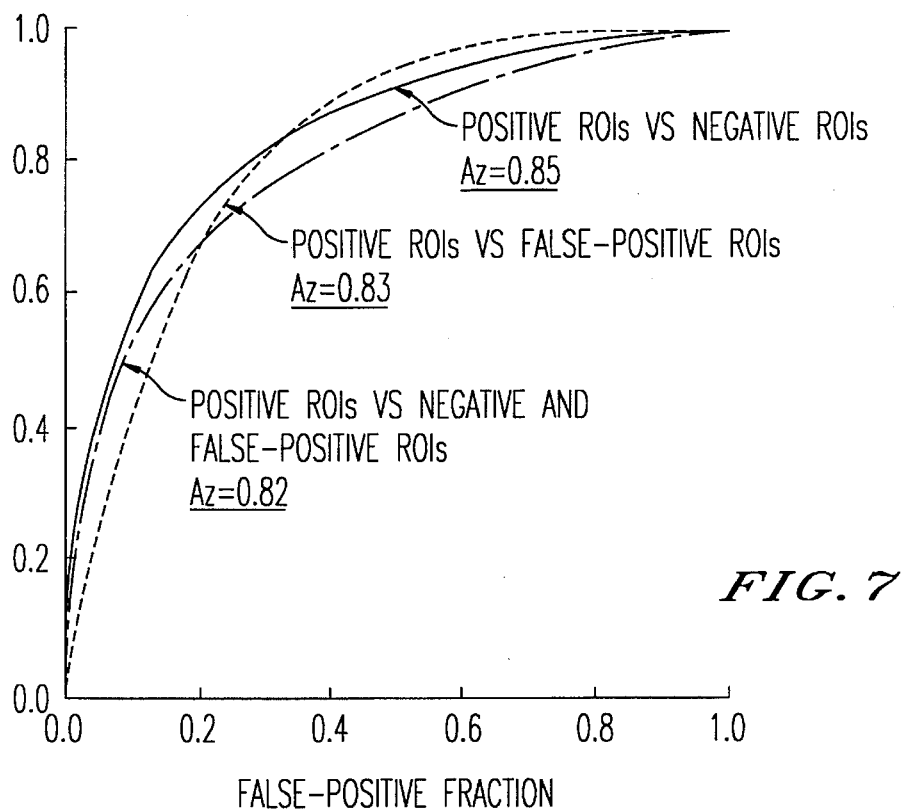
FIG. 7 is a graph illustrating the detection of clustered microcalcifications as a function of positive versus false-positive fraction in the spatial frequency domain using ROC analysis.

For more detailed analysis of the detection of clustered microcalcifications, each of the three groups, namely, distinguishing positive from negative ROIs, distinguishing positive from both negative and false-positive ROIs, were examined. FIG. 7 shows the ROC curves for the three comparisons. All three ROC curves are comparable and are at a fairly high level, whereas the value of $A_z$ for distinguishing positive from negative ROIs is slightly greater than are the values of $A_z$ for the other two categories. While the differences among the three ROC curves are not expected to be statistically significant, this result is consistent with an intuitive interpretation of the average power spectra illustrated in FIG. 5. Positive ROIs are separated from negative ROIs more readily than from false-positive ROIs.

In a modification of the first embodiment, an alternative approach to the detection of microcalcifications is in the spatial domain, i.e., background-corrected ROIs for both individual and clustered microcalcifications were used directly as input data to the neural networks without the Fourier transformation (see FIG. 4, middle row).

Using the database of 30 ROIs for individual microcalcifications, the consistency test again yielded 100% accuracy for classifying between positive and negative ROIs. This result indicates that the neural network is capable of learning patterns of individual microcalcifications in the spatial domain.

Figure 8:
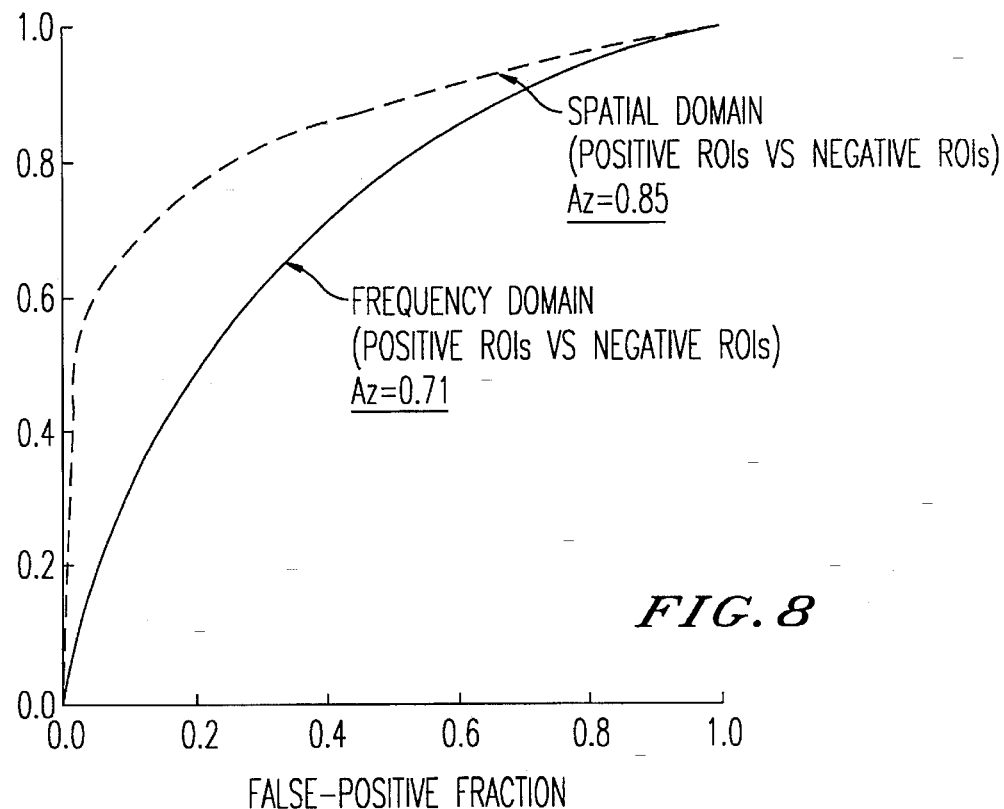
FIG. 8 is a graph illustrating the detection of individual microcalcifications comparing the spatial domain and the frequency domain.

In a test in which the jack-knife method was used, the neural network performed fairly well in detecting individual microcalcifications, yielding an $A_z$ value of 0.85. FIG. 8 shows the comparison of two ROC curves for the detection of individual microcalcifications in the spatial and the frequency domain. It is apparent that the network can detect individual microcalcifications in the spatial domain far better than in the frequency domain. This result was obtained partly because individual microcalcifications were centered at each of the ROIs.

Distinguishing clusters of microcalcifications was better performed in the frequency domain than in the spatial domain by the neural network method according to the invention. It should be noted that distinguishing individual microcalcifications was more accurate in the spatial domain than in the frequency domain. However, the detection of clustered microcalcifications instead of individual microcalcifications is a more realistic approach to the detection of breast carcinoma since it is inefficient and impractical for neural networks to detect microcalcifications initially and then identify clusters subsequently.

The ROC curve for distinguishing positive from false-positive ROIs, as shown in FIG. 6, indicates that the neural network, when applied to the results of the automated detection scheme, can eliminate approximately one half of the false-positive clusters while preserving 95% of the positive clusters (the ROC curve has a true-positive fraction (TPF) of 0.95, at a false-positive fraction (FPF) of 0.5). These values are determined by comparing the output of the neural network with a "gold standard" prepared by trained radiologists and considered to contain "true" microcalcifications. Thus, the neural network according to the invention can eliminate computer-reported false-positives from the prior art automated detection scheme and improve the overall detection efficiency.

Figure 9:
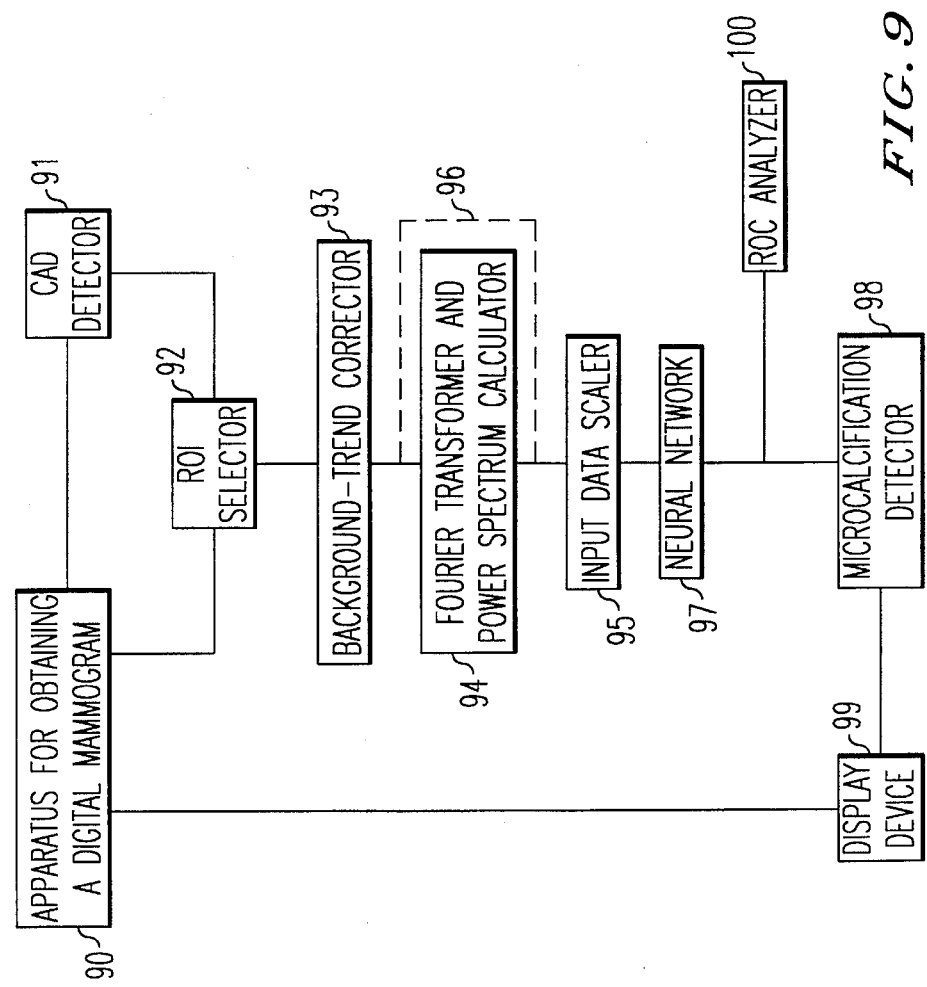
FIG. 9 is a block diagram of the system according to a first embodiment.

FIG. 9 illustrates the system for carrying out the method according to the first embodiment of the invention. The system of FIG. 9 includes an apparatus 90 for obtaining a digital mammogram, such as an x-ray device and laser scanner for digitizing a film mammogram produce a digital mammogram, and a CAD detector 91, such as described in U.S. Pat. No. 4,851,984 by Doi et al., for detecting microcalcifications in the digital mammogram. The output of CAD detector 91 is sent to ROI selector 92 which selects ROIs from the digital mammogram containing a suspected microcalcification based upon the information provided by CAD detector 91. The system further includes a background-trend corrector 93 for background-trend correcting an ROI selected by ROI selector 92, as described above, and Fourier transformer and power spectrum calculator 94 for calculating the Fourier transform and power spectrum from the background-trend corrected ROI. The input data scaler 95 scales the output of Fourier transformer and power spectrum calculator 94 for entry into neural network 97 which has been trained to detect microcalcifications. The background-trend corrector 93, Fourier transformer and power spectrum calculator 94, and input data scaler 95 could be implemented, for example, via a microprocessor programmed to carry out the background-trend correction, Fourier transformation and power spectrum calculation. In the case where detection is carried out in the spatial domain, the Fourier transformer 94 can be omitted as the Fourier transformation and the power spectrum calculation are not carried out, as indicated by the dashed line 96.

The output of the input data scaler 95 is fed to the neural network 97, the neural network 97 having a configuration as described above. The neural network 97 can be implemented in conventional fashion, such as a semiconductor device, a programmed microprocessor, or software. The output of the neural network 97 is input to ROC analyzer 100 for analyzing the training of neural network 97. ROC analyzer could also be a microprocessor programmed to carry out the ROC analysis, or be implemented as software. The output of the neural network 97 is also fed to a microcalcification detector 98 which detects the microcalcifications. The output by the neural network 97 contains a large value for a microcalcification cluster compared to other output corresponding to the input for false positives. The microcalcification detector 98 "detects" these areas and produces an input to a display 99 which allows overlay of the detected microcalcifications onto the digital mammogram. The display 99 could be a high resolution video screen to visually display the output results in terms of a grey scale, and an apparatus to generate a hardcopy of the output results (not shown).

Figure 10:
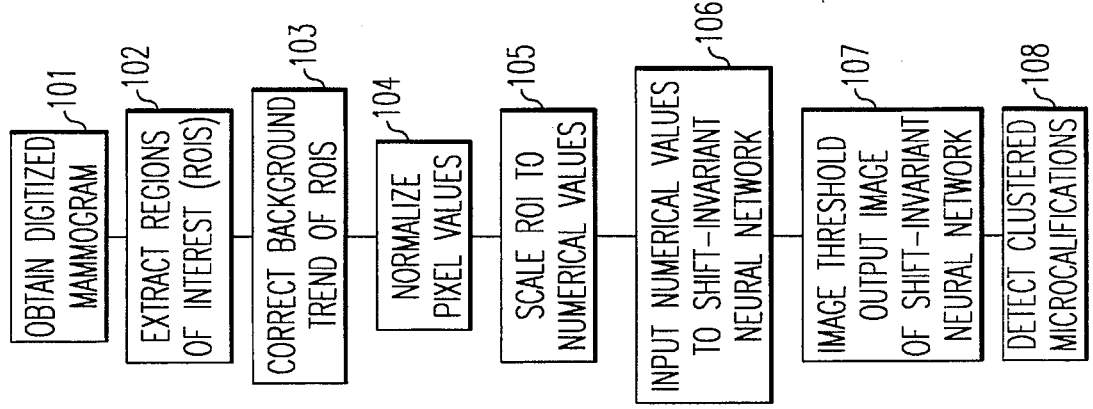
FIG. 10 is a flow chart of a method according to a second embodiment of the invention.

A second embodiment of the method according to the invention is shown in FIG. 10, and is described below. In this method, the number of the false-positive detections of the prior art CAD scheme can be significantly reduced by applying a novel shift-invariant neural network which contains higher generalizing ability than the conventional neural network. In the second embodiment, only clustered microcalcifications are detected, as clustered microcalcifications are of more interest in the detection of breast cancer, as described in the above discussion of the background of the invention.

First, suspect ROIs are obtained from a digital mammogram using a CAD scheme (steps 101 and 102), similar to that described above. Next, preprocessing of the ROI is performed which includes the background-trend correction (step 103) and pixel value normalization (step 104). The background-trend correction is used to isolate the signals from the nonuniform background included in a ROI image (as described above with respect to the first embodiment). For each selected ROI, a two-dimensional 3rd order polynomial curve fitting is used to estimate the background trend of the ROI. The estimated background trend is then subtracted from the original ROI to yield a background-trend corrected ROI (see FIG. 4).

After background-trend correction, the ROI is normalized by $$i(x, y) = \frac{i_t(x, y)N^2}{\sum_{x=1}^{N} \sum_{y=1}^{N} |i_t(x, y)|}$$

where $i_t(x,y)$ and $i(x,y)$ denote the ROI after background-trend correction and the ROI after normalization, respectively. $N^2$ is the total number of pixels in the ROI. The normalization is employed to maintain the variation of pixel values, that is related to the contrast of microcalcifications and the magnitude of radiographic mottle, in different ROIs within a relatively small range which can be provided by the summation of the absolute pixel values in a ROI, as expressed above. Note that the variation of pixel values can be very large if the average densities of ROIs are greatly different among different ROIs.

After scaling (step 105), the background-trend corrected and normalized ROI is then input to a shift-invariant neural network trained to detect microcalcifications (step 106) to produce an output ROI. The output ROI image of the shift-invariant neural network for a given input ROI image is first image thresholded (step 107) to yield a binary image at a certain threshold level of the output pixel value, in order to identify possible microcalcifications. For example, all areas having a pixel intensity value of 0.5 or greater can be assigned the value of 1, and all areas having a pixel intensity value less than 0.5 can be assigned a value of 0.

Figure 12:
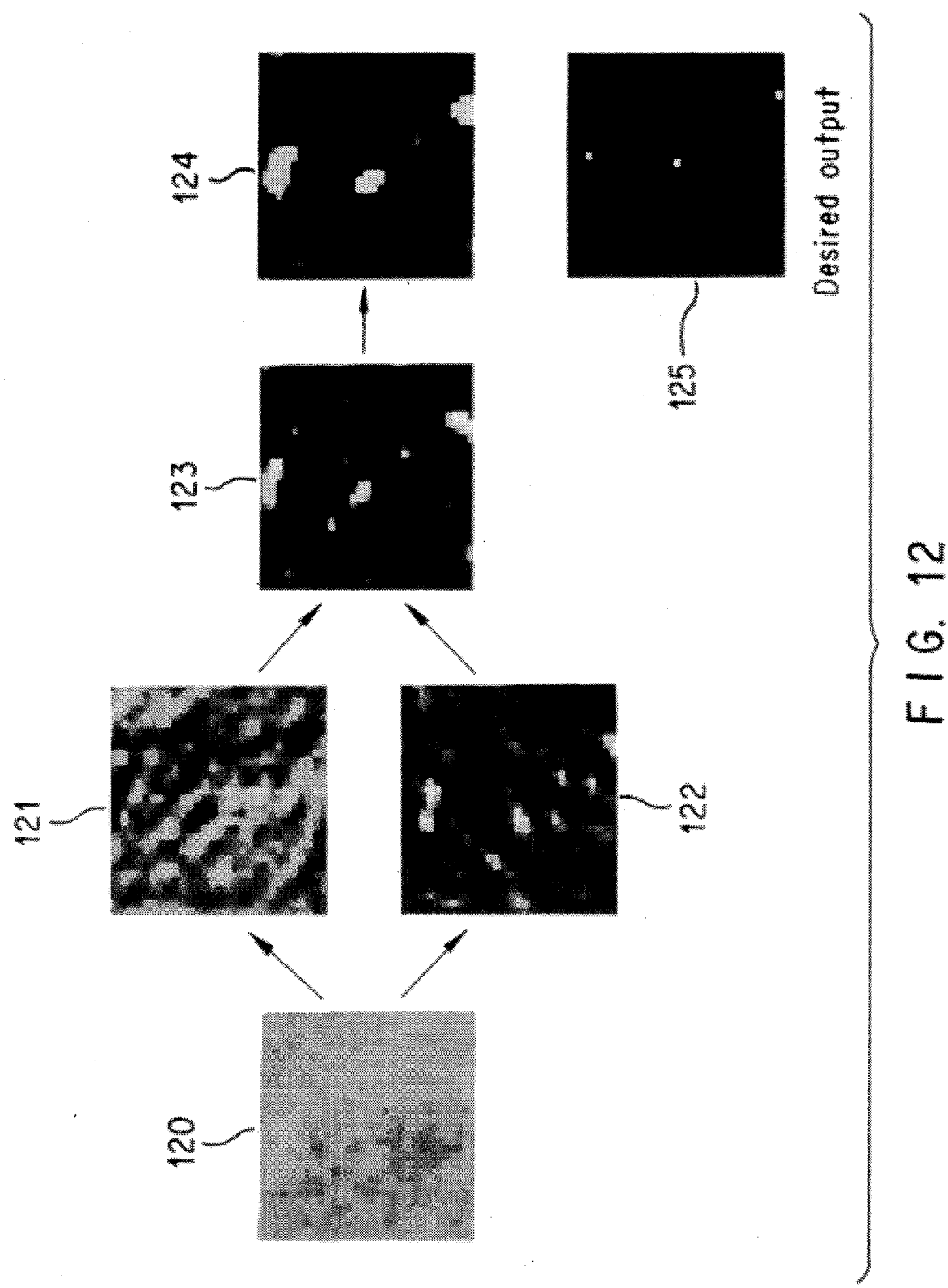
FIG. 12 is a diagram of ROIs at various points in the system according to the second embodiment.

The output image is then subjected to a counting operation to count, in terms of the number of microcalcifications included in each ROI, and detect the clustered microcalcifications (step 108). As shown in FIG. 12, ROI 124 contains a number of "white" areas which correspond to detected microcalcifications. If the number of "detected microcalcifications" in the output ROI image is equal to or greater than a certain number, the ROI is considered a positive ROI, i.e., an ROI with clustered microcalcifications; otherwise, the ROI is considered negative. The performance of the system based on cluster criterion is described below in Table III.

Figure 11A:
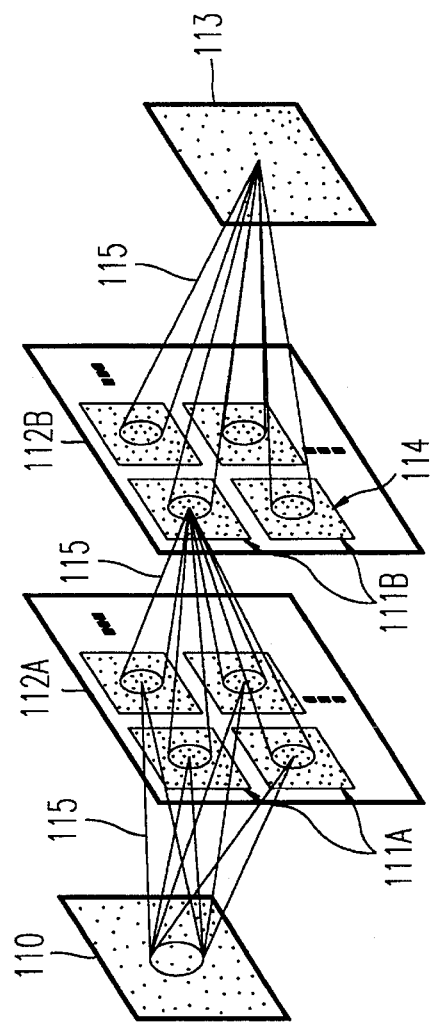
FIGS. 11A and 11B are schematic diagrams of the neural network according to a second embodiment and the interconnections of the neural network, respectively.
Figure 11B:
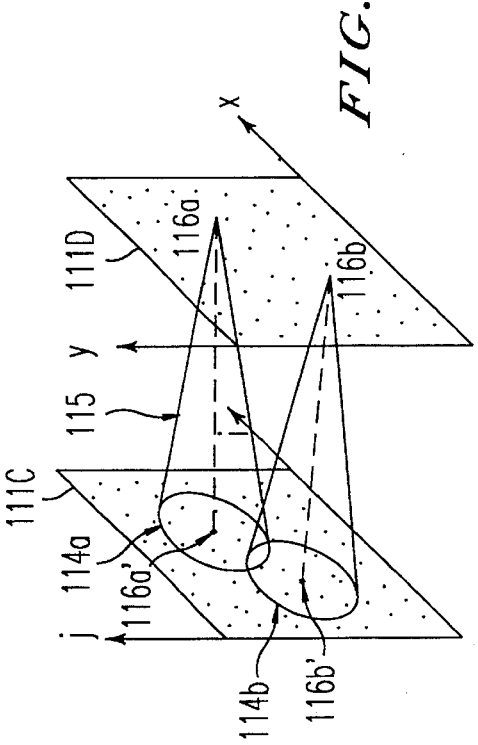

A shift-invariant neural network has been described by Zhang et al. in "Parallel Distributed Processing Model with Local Space-invariant Interconnections and its Optical Architecture" Appl. Opt. 29, 4790–7 (1990), and "Image Processing of Human Corneal Endothelium Based on a Learning Network", Appl. Opt. 30, 4211–7 (1991). The shift-invariant neural network of the second embodiment is a layered feed-forward neural network with local, spatially-invariant interconnections as illustrated in FIG. 11A and 11B. The basic structure of the shift-invariant neural network is similar to that of the Neocognitron model developed by Fukushima (see Fukushima et al., "Neocognition: A Neural Network Model for a Mechanism of Visual Patter Recognition", IEEE Trans. Sys. Man and Cybernetics, SMC-13, 826–43 (1983)). However, the shift-invariant neural network of the invention is a feed-forward neural network without lateral interconnections and feedback loops that are included in the Neocognitron. Furthermore, instead of the winner-take-all training algorithm, the error back-propagation (EBP) is used as the training algorithm in the shift-invariant neural network.

As shown in FIG. 11A, units in the input layer 110 and output layer 113 correspond to pixels of the input and output images, respectively. The input images, in the case of this embodiment, are the ROIs selected by the CAD scheme. Units in any single hidden layer 112A or 112B are respectively divided into groups 111A and 111B. Every unit in a subsequent layer is connected with the units of a small region in every group in the preceding layer via weighted links 115. The weights 115 are described in more detail below in FIG. 11B. The small circles 114 shown in FIG. 11A illustrate the small predefined connection regions called the receptive field of the units. The receptive areas 114 are shown as circles for illustration purposes only, while actually the receptive fields 114 are square or rectangular groups of pixels in the groups 111A or 111B. The size of the receptive fields 114 are determined empirically. Table II below provides examples of number of units, groups and size of the receptive field for the system according to the second embodiment of the invention. As is apparent from Table II, the number of units in successive layers decreases.

To obtain the shift-invariant responses, connection weights between any two groups in two layers are constrained to be shift-invariant. FIG. 11B illustrates the shift-invariant interconnections between two groups in two successive layers. As shown in FIG. 11B, each unit in one group of the subsequent layer (units 116a and 116b in group 111D, for example) receives input from the receptive field centered at the corresponding unit in the preceding layer (units 116a' and 116b' having respective receptive fields 114a and 114b in group 111C). The groups 111C and 111D are labeled as group p in the lth layer and group q in the (l+1)th layer, and have been provided with coordinate reference systems i-j and x-y, respectively, for the analysis that follows. The distribution (or pattern) of the connection weights of any unit in the same group is kept exactly the same. In general, if w(i,j;x,y) denotes connection weight between the unit at the location (i,j) in the preceding layer and the unit at (x,y) in the subsequent layer, the shift-invariant connection weights can be formulated as follows:

$$w(i,j;x,y) = w(i-x, j-y)$$

In this way, each unit contains exactly the same weights distribution, and thus each unit is assured to operate in the same way over its receptive field. Therefore, the response in one group of the subsequent layer is not dependent on the location of the pattern in the preceding layer, which may include the input layer. Consequently, the interconnection between the units in two groups can be considered to represent a spatial filter with the connection weights as its component and with the size of the receptive field.

In the case of multigroup and multilayer neural networks as shown in FIG. 11A, units in the same layer but belonging to a different group have the same size of receptive field, but different pattern of connection weights. To avoid the effect of the edges in the input images, the number of the units in each group of subsequent layer is reduced depending on the size of the receptive field. Assume that the number of the units of a group in the lth layer is N×N and the receptive field size in the (l+1)th layer is M×M, the number of the units of the group in the (l+1)th layer should be (N−M+1)× (N−M+1). An example of the configuration of the second embodiment is providing in Table II as follows:

TABLE II

| Layer Number | 1 | 2 | 3 | 4 |
|---|---|---|---|---|
| Number of Units | 49 × 49 | 43 × 43 | 37 × 37 | 31 × 31 |
| Number of Groups | 1 | 2 | 1 | 1 |
| Size of Receptive Field | — | 7 × 7 | 7 × 7 | 7 × 7 |

The input of the unit (x,y) is defined by $N_p^l(x,y)$ the connection weights by $W_{p,q}^l(x,y)$ and the output of the unit by $O_p^l(x,y)$, where l=(1,2, ... L) layer number, p=(1,2, ... $P^l$) group number in the lth layer, and q=(1,2, ... $P^l+1$) group number in the (l+1)th layer.

With the feed-forward propagations of signals in the network, the outputs in the subsequent layer are given by summation of "filtered" patterns, which are obtained by convolution of the patterns in different groups of the preceding layer with a number of filters (or connection weights), followed by pointwise thresholding, namely:

$$N_q^{l+1}(x, y) = \sum_{p=1}^{P^l} (O_p^l(x, y) * W_{p,q}^l(x, y)),$$

$$O_q^{l+1}(x, y) = f(N_q^{l+1}(x, y) + b_q^{l+1}),$$

where the symbol "*" denotes the operation of convolution and f(x) is the sigmoid-like nonlinear function to denote the pointwise thresholding. In this study, a bipolar sigmoid-like function as follows was used:

$$f(x) = \frac{2}{1 + \exp(-x)} - 1.$$

In the second embodiment, the conventional error-back-propagation algorithm (EBP) is modified for training with the shift-invariant interconnections. The modified EBP training algorithm for the shift-invariant neural network is as follows. The error-back-propagation (EBP) training algorithm has been modified to meet the requirement for the structure of the shift-invariant neural network and to maintain the connections as shift-invariant. Let the change of the weight and the bias in the training phase be $\Delta w_{p,q}^l(x,y)$ and $\Delta b_p^l$ respectively. The EBP training algorithm in the shift-invariant neural network can be modified as follows:

$$\Delta W_{p,q}^l(x, y) = \eta \delta_q^{l+1}(x, y) * O_p^l(x, y) + \alpha W_{p,q}^l(x, y)$$

$$\Delta b_p^l = \eta \sum_i \sum_j \delta_p^l(x, y) + \alpha b_p^l$$

$$\delta_p^l(x, y) = f'(N_p^l(x, y) + b_p^l) \sum_q [\delta_q^{l+1}(x,y) * \tilde{W}_{p,q}^l(x, y)]$$

$$\tilde{W}_{p,q}^l(x, y) = W_{p,q}^l(-x, -y)$$

where in the case of the last layer, $$\delta_l^L(x,y) = f'(N_l^L(x,y) + b_l^L)[T(x,y) - O_l^L(x,y)]$$

where $f'(x)$ denotes the derivative of $f(x)$, and $T(x,y)$ is the desired output image. The factors η and α indicate the learning rate and the constant factor of the moment term, respectively.

The training error related-to the differences between the desired outputs and the actual outputs for all the input training images is determined by $$E = \sum_i \sum_{x,y} (t^i(x,y) - o^i(x,y))^2,$$

where $t^i(x,y)$ and $o^i(x,y)$ denote the desired output image and the actual output image, respectively, of the neural network for the training input image i.

The actual training of the shift-invariant neural network of the second embodiment for the detection of individual microcalcifications will be described. For an input ROI containing microcalcifications, the desired output image of the network was designed such that the output of a unit in the output layer is 1, only if the corresponding unit in the input layer is at the center of a microcalcification, and −1 otherwise. FIG. 12 illustrates this process. The input layer ROI 120 is processed as described above to obtain ROIs 121 and 122 of the first hidden layer. ROIs 121 and 122 are processed to obtain ROI 123 of the second hidden layer, and ROI 123 is processed to obtain the output layer ROI 124. In ROI 124 the white areas represent the detection of possible microcalcifications. The desired output of ROI 125 is prepared by a radiologist and consists of a black dot at the location of a "true" microcalcification. The ROI 124 is an output image where all units having a brightness greater than a certain value, for example, 0.5, are considered to indicate the presence of a microcalcification, and all units having a brightness less than the certain value correspond to normal background. Reversing the polarity will allow a direct comparison of the neural network output with the desired output. With continued training, the output of the neural network should coincide with the desired output. In the present invention, the efficiency of the training process is nearly 100%, resulting in the detection of all actual microcalcifications.

As an example of the training process used in accordance with the invention, all weights start with random values between −0.3 and 0.3. The values of −0.9 and 0.9 are typically used as the convergence targets of −1 and 1, respectively. The learning rate η and the constant factor of the moment term α were 0.01 and 0.9, respectively. The training is terminated when there is no significant decrease in the training error as the training trial increases. The training process is typically terminated at 4500–6000 trials.

The performance of the method according to the second embodiment including the use of the neural network was evaluated based on a jack-knife test and ROC analysis. All of the image data in the database described above (168 ROIs of 32×32 pixels from 34 digital mammograms) were used for training and testing the shift-invariant neural network. For each category, i.e., positive, false-positive and normal ROIs, one half of the cases were selected randomly from the database for training, and the other half were used for testing of the trained network. This evaluation method was repeated five times by changing the cases for training and testing to examine the effect of the case selection on the overall performance. For each of the five combinations of the training and testing data, the true positive fraction (TPF) and the false positive fraction (FPF) of the classification decisions made by the trained shift-invariant neural network were calculated at various threshold levels by comparing with the desired output data for clustered microcalcifications determined by trained radiologists.

Next, ROC analysis used to analyze independently the results obtained from the five testing data sets. The average area under ROC curve $A_z$ and the average minimum FPF at the TPF of 1.00 for the five data sets are employed as measures of the performance of the network. In addition, the standard deviations of the $A_z$ and the minimum FPF are considered as indicators of the generalization of the result. Generally, the larger the $A_z$ and the less the standard deviation, the greater the overall performance of a network. Also note that the lower the FPF (at TPF=1.00), the more the false positive ROIs can be eliminated by the network while preserving all of the positive ROIs.

In evaluating the neural network system, the effects of the cluster criterion, the structure of the neural network, and the pixel value normalization on the performance of the shift-invariant neural network were investigated. In addition, the performance of the shift-invariant neural network system was compared with that of the conventional neural network used in the first embodiment.

First, the effect of the cluster criterion (the number of "detected" microcalcifications in the ROI) on the overall performance of a network having a structure code 1211_7 was examined. Here, codes are used to describe the network structures. The code 1211_7, for example, indicates that the neural network is a four-layer network with one group in the input layer, two in a second layer, one in a third layer, one in the output layer and the filter size (receptive field size) in each layer is 7×7. The detailed configuration of the structure 1211_7 is summarized in Table II, where layers 1–4 correspond respectively to 1211. Table III shows performance measures ($A_z$ using ROC analysis and FPF for TPF=1.00) for the neural network according to the invention for various cluster criteria.

TABLE III

| Cluster Criterion | $A_z$ | FPF |
| --- | --- | --- |
| 1 | 0.88 ± 0.04 | 0.50 ± 0.11 |
| 2 | 0.91 ± 0.02 | 0.43 ± 0.10 |
| 3 | 0.91 ± 0.03 | 0.48 ± 0.19 |
| 4 | 0.90 ± 0.05 | 0.56 ± 0.21 |
| 5 | 0.88 ± 0.05 | 0.68 ± 0.21 |

Table III shows that for a detection threshold (certain number) of 2 microcalcifications optimal results can be achieved (maximum $A_z$ indicating accurate prediction with minimal FPF).

The performance of the network for the particular ROI size (31×31 pixels in the output layer, as shown in Table II) indicates the highest $A_z$ value and the lowest FPF, when the cluster criterion is two. When the cluster criterion is larger than two, some of the subtle cases containing only two microcalcifications were missed. For the cluster criterion equal to one, the results were biased by the effect of a large noise.

The effect of the structure of the neural network, i.e., the number of layers, groups, and the size of filter in each layer, on the overall performance was also studied, as indicated in Table IV. Table IV shows the dependence of $A_z$ value and the FPF (at TPF=1.00) on the network structure used in distinguishing positive ROIs from false-positive ROIs.

TABLE IV

| Network structure | $A_z$ | FPF |
| --- | --- | --- |
| 11_7 | 0.85 ± 0.03 | 0.64 ± 0.08 |
| 111_7 | 0.89 ± 0.05 | 0.44 ± 0.21 |

TABLE IV-continued

| Network structure | $A_z$ | FPF |
|---|---|---|
| 121_7 | 0.87 ± 0.03 | 0.54 ± 0.15 |
| 1111_7 | 0.90 ± 0.03 | 0.59 ± 0.13 |
| 1211_7 | 0.91 ± 0.02 | 0.43 ± 0.10 |
| 1211_5 | 0.88 ± 0.03 | 0.41 ± 0.10 |
| 1211_9 | 0.87 ± 0.03 | 0.63 ± 0.21 |

Seven different network structures were investigated. For simplicity, the same filter size (receptive area size) was chosen for all of the layers in the network. In order to compare the results of the second embodiment with those of the first embodiment, the output image size of the shift-invariant neural network was chosen to be 31×31 pixels (odd number of pixels is preferred for the determination of a "center" pixel of a ROI) while the input ROI size is determined by the structure of the network.

All of the structures indicated in Table IV were trained and tested with five different combinations of the 56 positive false positive ROIs in the database. Table IV also illustrates the average $A_z$ values and their standard deviations as well as the minimum FPF at the TPF of 1.00. It should be noted in Table IV that the structure 1211_7 has the largest $A_z$ and the smallest standard deviation among all of the structures investigated. The structure 1211_7 also has the lowest FPF except the structure 1211_5. However, since the difference of the FPFs between 1211_7 and 1211_5 is very small, but $A_z$ of 1211_7 is considerably larger than that of 1211_5, the network structure 1211_7 was considered to provide optimal detection.

As an illustration of how the 1211_7 network works, refer again to FIG. 12 which shows one of the input testing ROIs 120, the corresponding desired output image 125, and the actual responses of the units in each layer after 5000 training trials (ROIs 121–124). In FIG. 12, microcalcifications in the processed images in the group 1 and 2 (121 and 122) of the second layer are enhanced with the reversed contrast and suppressed, respectively. Microcalcifications appear to be clearly extracted in the third layer (123), and are further enhanced in the final output layer (124).

For the network having the structure 1211_7, the performance of the network with and without the normalization are shown in Table V.

TABLE V

| Preprocessing | $A_z$ | FPF (TPF = 1.00) |
|---|---|---|
| pixel value normalization | 0.91 ± 0.02 | 0.43 ± 0.10 |
| no pixel value normalization | 0.87 ± 0.04 | 0.60 ± 0.14 |

By preprocessing the input images with the pixel value normalization, the FPF can be reduced from 0.60 to 0.43, and $A_z$ can be improved from 0.87 to 0.91. Thus, it is apparent that the network with the normalization is superior to that without the normalization. This is probably due to the fact that the normalization processing can amplify the contrast of subtle microcalcifications, and thus the neural network is trained more effectively with normalization of the input image.

In the first embodiment where a conventional neural network was used, ROI groups were examined for distinction between the two kinds of ROIs, namely, positive ROIs versus false-positive ROIs, positive ROIs versus negative ROIs, and positive ROIs versus both negative and false-positive ROIs (see FIG. 7). In order to compare the results of the second embodiment with those of the first embodiment, the shift-invariant neural network for the same groups of ROIs was examined. The network having the structure 1211_7 with the pixel value normalization was used. The average $A_z$ values and their standard deviation derived from the five combinations are shown in Table VI, where $A_z$ values obtained for the first embodiment are also shown for comparison.

TABLE VI

| | Second Embodiment $A_z$ | First Embodiment $A_z$ |
|---|---|---|
| Positive ROIs versus false-positive ROIs | 0.91 ± 0.02 | 0.83 ± 0.02 |
| Positive ROIs versus Negative ROIs | 0.93 ± 0.02 | 0.85 ± 0.02 |
| Positive ROIs versus Negative and false-positive ROIs | 0.92 ± 0.02 | 0.82 ± 0.02 |

It is evident from Table VI that the method using the shift-invariant neural network of the second embodiment performs substantially better than the conventional neural network of the first embodiment.

Figure 13:
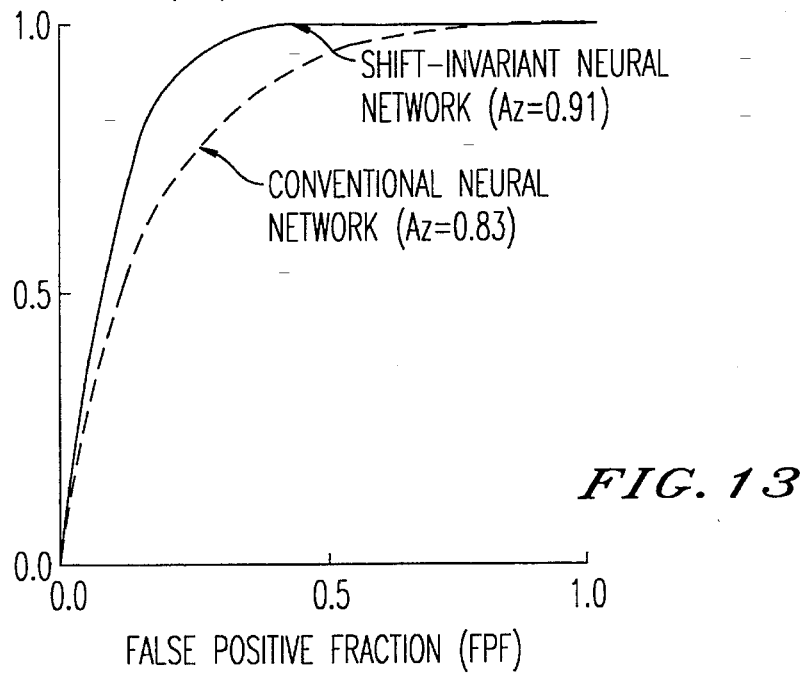
FIG. 13 is a graph comparing the neural networks of the first and second embodiments using ROC analysis.

FIG. 13 shows the comparison of the average ROC curves for distinguishing positive ROIs from false-positive ROIs obtained for the first and second embodiments. It is apparent that the shift-invariant neural network of the second embodiment performs noticeably better than the conventional neural network of the first embodiment. With the shift-invariant neural network method and system, about 55% of false positive ROIs identified by the automated computer scheme can be eliminated without any loss of the positive ROIs. With the conventional neural network method and system, however, only about 20% of false positive ROIs can be eliminated while preserving all of the positive ROIs.

The better performance of the shift-invariant neural network method and system compared with that conventional neural network method and system can possibly be attributed to the use of ROI in the spatial domain as the input, and subsequently the "strong" independence of the shift-invariant neural network method and system to the shape of the clustered microcalcifications. Here, the shape of a clustered microcalcifications may be defined by the relative locations of microcalcifications and the orientation of the cluster as well as the number of microcalcifications in the cluster.

In testing the first embodiment, it was found that the performance of the conventional neural network on individual microcalcifications in the spatial domain was better than that in the frequency domain (power spectrum) when each microcalcification is centered in the input layer (see FIG. 8). This is probably related to somewhat complicated differences in the two approaches employed in different domains, i.e., individual microcalcifications are centered as input in the spatial domain whereas the power spectrum is spread relatively widely in the frequency domain. Thus, the "signal-to-noise ratio" of entry data for individual microcalcifications to the neural network would be greater in the spatial domain than in the frequency domain. However, the performance of the conventional neural network for the detection of clustered microcalcifications was superior in the frequency domain than in the spatial domain. This result was explained by the fact that the Fourier transform in obtaining the power spectrum can "center" the frequency contents of clustered microcalcifications which are spread widely and randomly in the spatial domain. Indeed, the conventional neural network in the spatial domain was not able to detect any of clustered microcalcifications in the testing set after training.

The shift-invariant neural network method and system makes it possible to use an ROI in the spatial domain as input so that the inherent superior capability of a neural network in detecting individual microcalcifications can be maintained. This is probably the reason why the performance of the shift-invariant neural network in detecting clustered microcalcifications was better than that of the conventional neural network, which was useful only in the frequency domain. In addition, the connection of units in the shift-invariant neural network are localized, i.e., a unit is only connected with the units within a small region in the preceding layer. Therefore, a local variation such as artifacts in the input image does not affect the outputs of the units whose receptive fields do not include the local variation. In addition, the final decision of classifying an input ROI as positive or negative is based on whether the number of detected microcalcifications is above a given criterion regardless of the relative locations of each microcalcification and thus the orientation of the cluster (see Table III). Therefore, the shift-invariant neural network method and system for the detection of clustered microcalcifications is highly independent of the shape of the clustered microcalcifications.

Figure 14:
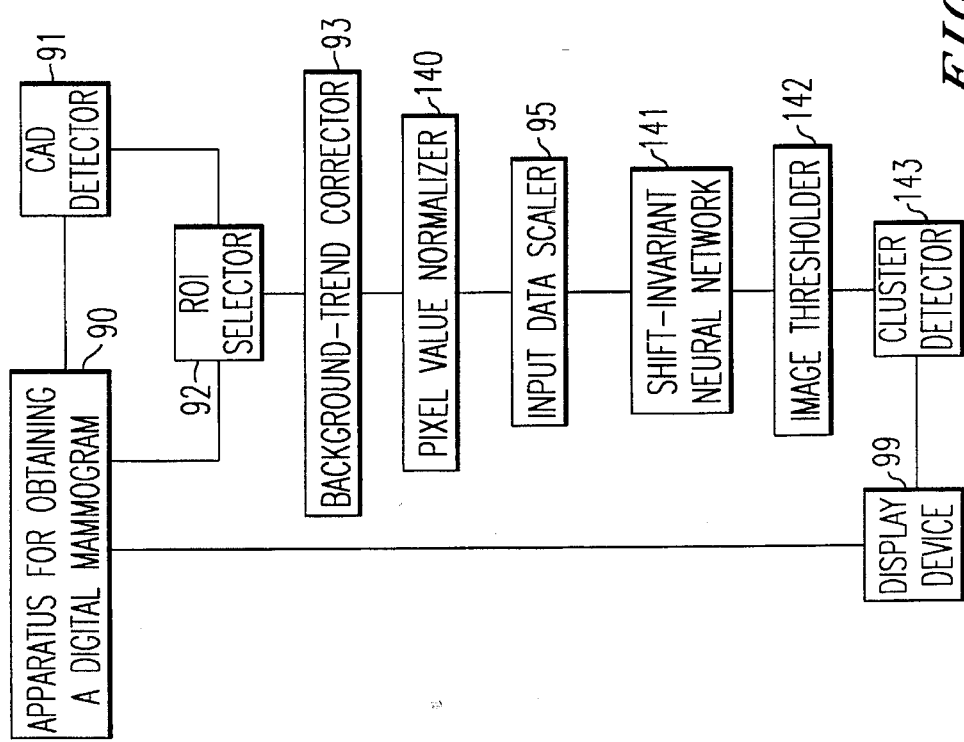
FIG. 14 is a block diagram of the system according to the second embodiment of the invention.
Figure 15:
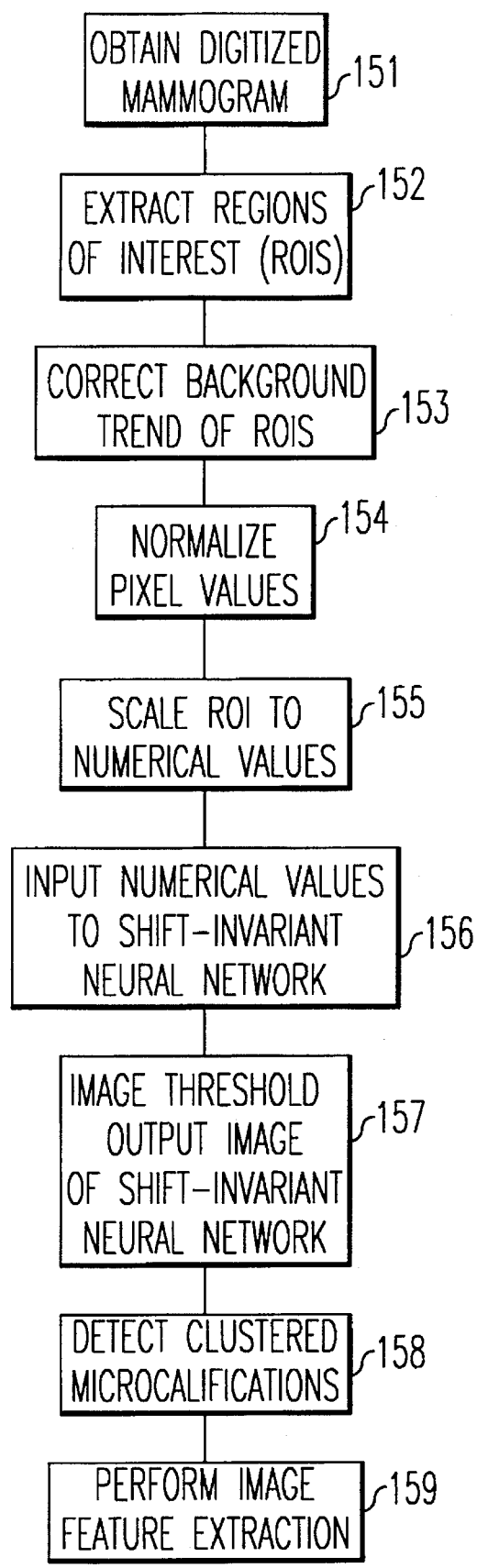
FIG. 15 is a flow diagram of a third embodiment of the method according to the invention.

The system according to the second embodiment will be described. As shown in FIG. 14, the system according to the second embodiment includes an apparatus for obtaining a digital mammogram 90, which can be implemented as described above in connection with the first embodiment. The digital mammogram is input to a CAD detector 91 for detecting suspect clustered microcalcifications. The output of the CAD detector 91 is fed to an ROI selector 92, which selects the suspect ROIs from the digital mammogram. The suspect ROIs are input to a background-trend corrector which applies a two-dimensional third order polynomial curve fitting to isolate the signals from the nonuniform background included in a ROI, as described above. The background-trend corrected ROI is then normalized using pixel normalizer 140 to maintain the variation of pixel values, as also described above. The pixel normalizer can be implemented using a programmed microprocessor, for example.

The normalized and background-trend corrected ROI is then input to an input data scaler 95 for converting the ROI into numerical form for input into shift-invariant neural network 141. The shift-invariant neural network can be implemented in conventional fashion, such as a semiconductor device or as software. The shift-invariant neural network 141 has been trained to detect microcalcifications and produces an output ROI indicating detected clustered microcalcifications. This output image is then image thresholded by image thresholder 142 to yield a binary image at a desired image threshold level, and then the output of image thresholder 142 is fed to a cluster detector 143 which counts the number of microcalcifications included in each ROI, as described above, and determines whether the ROI is considered positive or negative, based upon whether the number of detected microcalcifications exceeds a certain number, as described above in Table III. The cluster detector 143, which is typically implemented using software or a programmed microprocessor, detects the microcalcifications and creates an output which is fed to a high-resolution display device 99 to indicate on the original digital mammogram, i.e. by overlaying, the detected microcalcifications.

It should be pointed out that the pixel normalizer 140 can be omitted from the system shown in FIG. 14. Eliminating the pixel normalizer 140 reduces the complexity of the system but results in slightly lower detection accuracy, as illustrated in Table V.

Referring to FIGS. 15–18, a third embodiment of the invention will be described. The method (FIG. 15) consists of the method of the second embodiment (steps 101–108 have been renumbered as steps 151–158, respectively) but includes a step 159 of image feature extraction of ROIs selected as having suspected microcalcifications. Feature extraction techniques may include the determination of contrast, size (or area) of the microcalcification, texture measures such as the first moment of the power spectrum of the ROI, edge gradients, cumulative edge gradients, the average and standard deviation of edge-gradient-orientation histogram of the ROI, and the average optical density of the ROI. The extraction of such features from a digital radiograph is described in copending application Ser. No. 07/915, 631, the disclosure of which is herein incorporated by reference.

Using feature extraction after the use of the shift-invariant neural network is based on the idea that a large fraction of the false-positive ROIs can be removed by using the shift-invariant neural network and thus it becomes possible to employ a more accurate feature thresholding scheme for distinction between the positive and remaining false-positive ROIs.

Figure 16A:
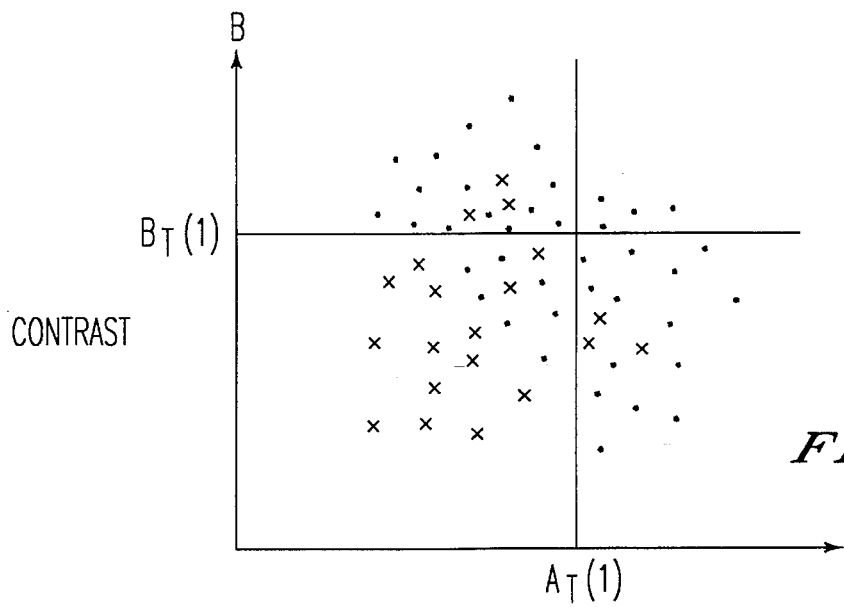
FIGS. 16A, 16B, 16C and 16D are graphs illustrating feature thresholding in conjunction with the method according to the third embodiment of the invention.

The use of the feature extraction technique, in particular feature thresholding, will be illustrated in conjunction with FIGS. 16A–16D. In FIG. 16A, the "x" represents a true clustered microcalcification. The dots represent false-positive detections by CAD detector 91. FIG. 16A shows thresholds $A_T(1)$ and $B_T(1)$ which eliminate a great number of the false-positive detections. However, these thresholds also undesirably eliminate several of the true positive detections. The feature thresholding of FIG. 16A produces a TPF of $14/20$ (70%) and includes seven false-positive detections (the area of the curve below threshold $B_T(1)$ and to the left of threshold $A_T(1)$). The TPF exhibited by the feature thresholding of FIG. 16A is relatively low.

Figure 16B:
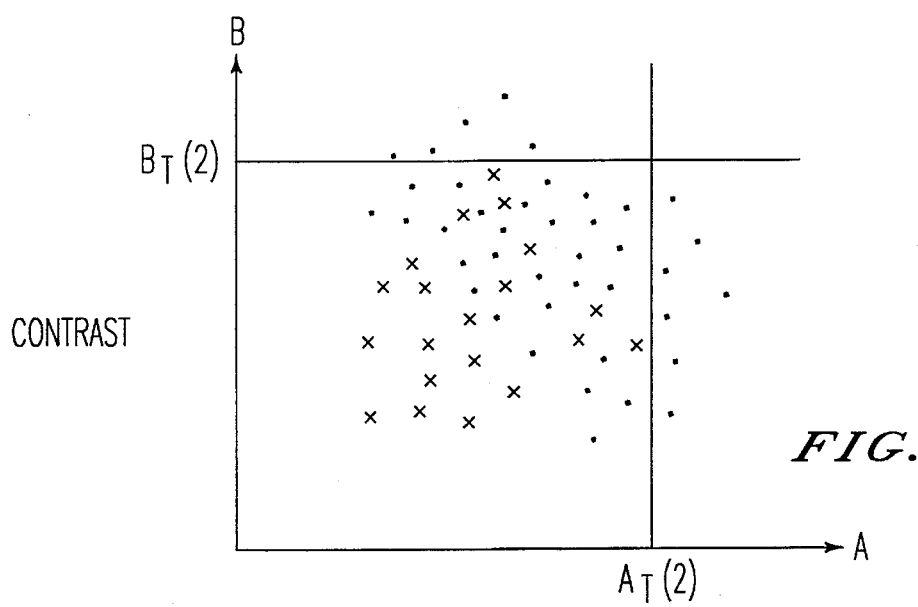

FIG. 16B illustrates thresholds $A_T(2)$ and $B_T(2)$ which provide a TPF of $20/20$ (100%), but includes a very high number (28) of false-positive detections. The high number of false-positive detections is undesirable.

Figure 16C:
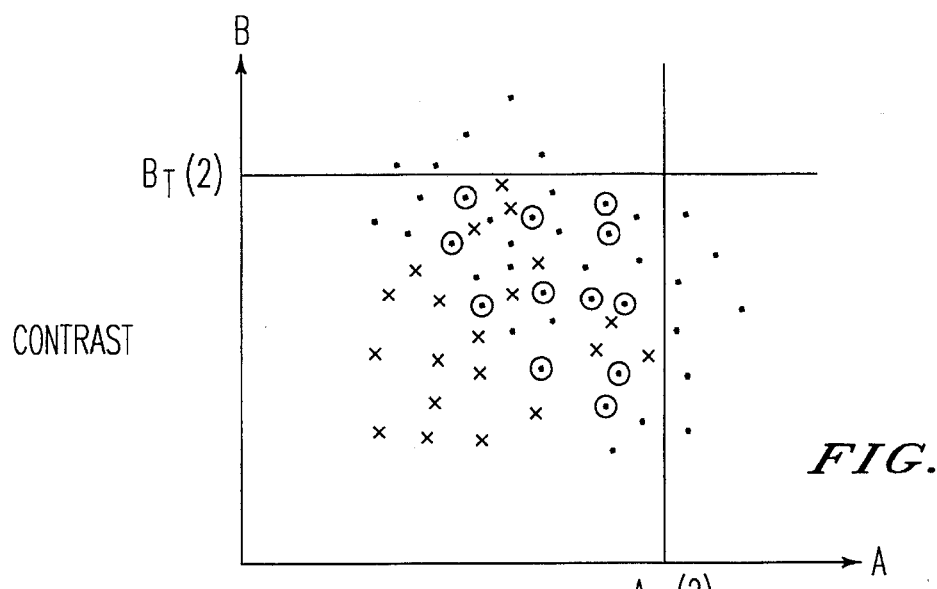

The use of the neural network 141 in conjunction with the feature extraction technique is illustrated in FIG. 16C. The dots which are circled are false-positives which have been removed by shift-invariant neural network 141. Using the thresholds $A_T(2)$ and $B_T(2)$, a TPF of $20/20$ (100%) can be realized while reducing the number of false-positive detections to 16. The neural network has removed twelve of the false-positive detections. It should be noted the neural network has correctly detected each of the "true" microcalcifications.

Figure 16D:
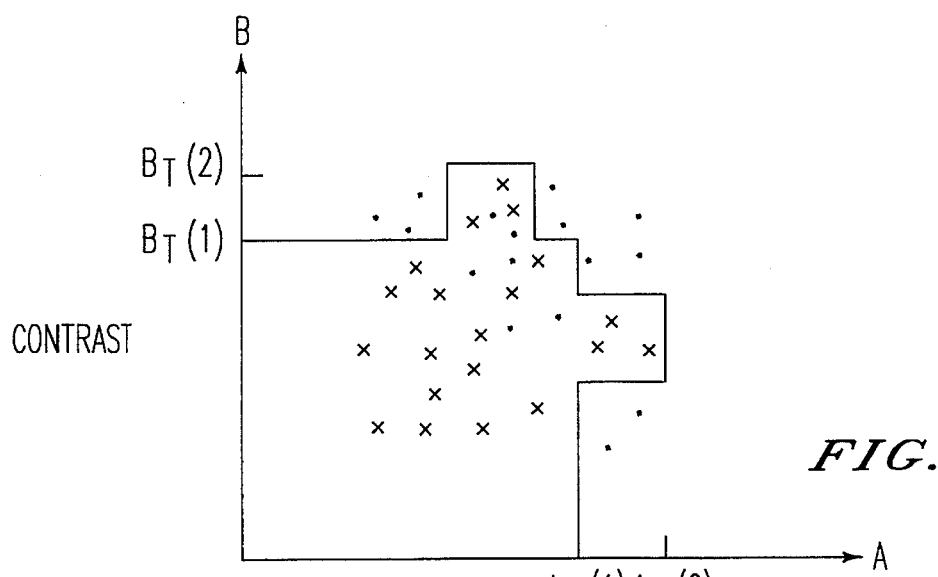

Eliminating the twelve false-positives removed by the neural network results in the distribution shown in FIG. 16D. FIG. 16D also illustrates a more complex feature thresholding which is a combination of the thresholds $A_T(1)$, $A_T(2)$, $B_T(1)$ and $B_T(2)$. Using this complex feature thresholding, an additional six false-positives can be removed while maintaining all of the "true" microcalcifications. Thus, it is apparent the combination of detection using shift-invariant neural network 141 and feature thresholding can significantly improve the detection by maintaining a TPF of 100% while eliminating a large portion of the false-positive detections.

The thresholds illustrated in FIGS. 16A–16D are empirically derived. The microcalcifications detected using the feature extraction techniques are compared with the "true" microcalcifications in a digital mammogram prepared by a trained radiologist and those detected by the shift-invariant neural network. By using this feature thresholding technique on several test digital mammograms, appropriate thresholds can be determined which can maintain a TPF of 100% while eliminating a large number of false-positive detections.

Figure 17C:
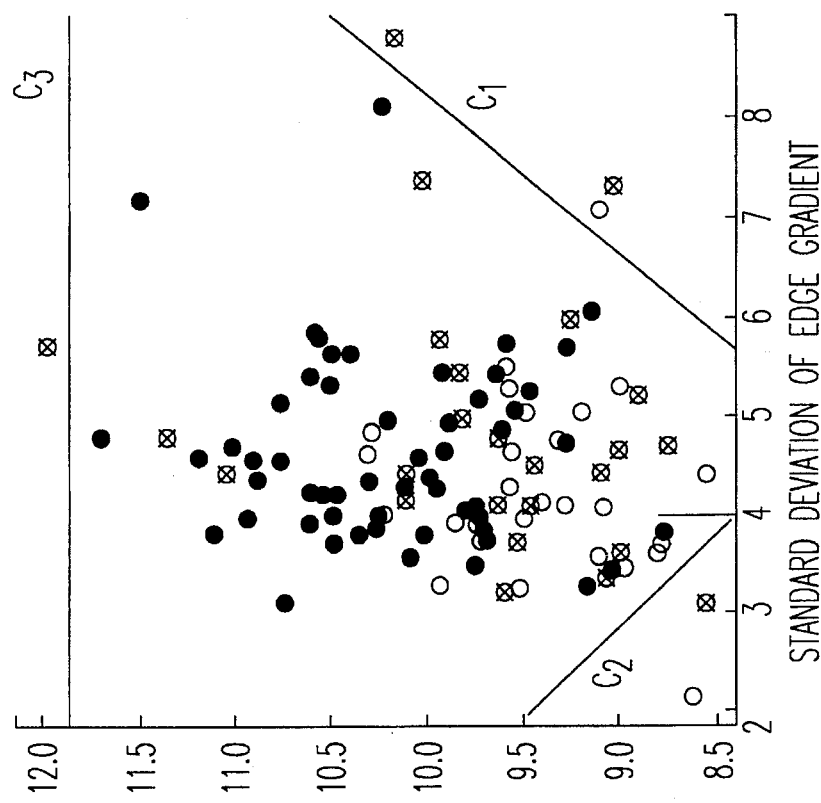
FIGS. 17A, 17B and 17C are graphs illustrating examples of feature extraction in the method according to the third embodiment of the invention.
Figure 17A:
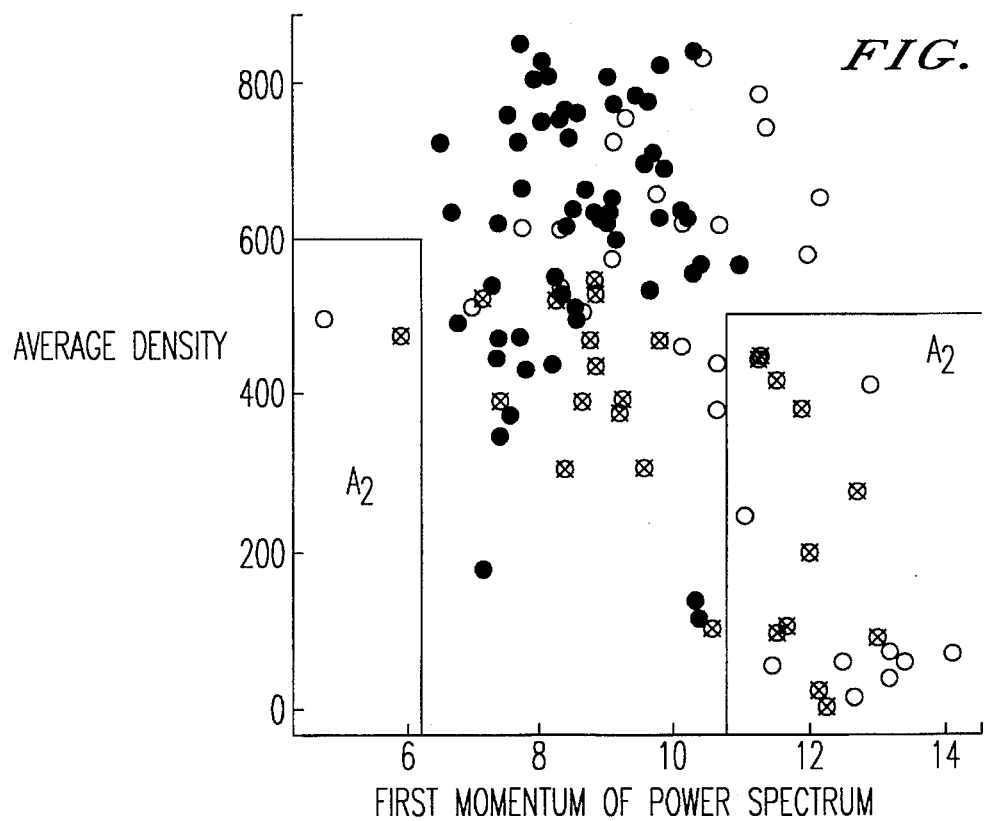
Figure 17B:
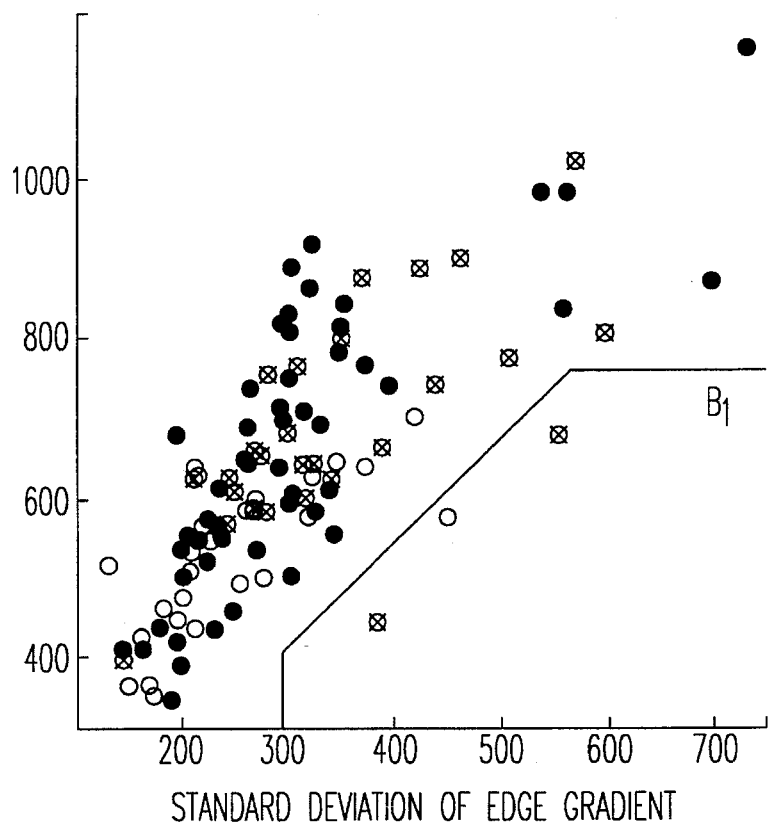

A second example of using feature extraction techniques with data from the above-mentioned database is provided by FIGS. 17A–17C. In FIG. 17A, the black dots represent positive clustered microcalcifications, open dots represent false-positives removed by the neural network, and dots having an "x" superimposed thereon represent remaining false-positives. The data used is the 56 positives and 56 false-positives described above. The 30 false positives were removed by the shift-invariant neural network. Applying the feature thresholds $A_1$ and $A_2$ can remove 11 and 1, respectively, additional false-positives.

Different feature extraction also can remove false-positives. FIG. 17B shows a feature threshold $B_1$ which removed two false-positives. The false-positives removed are in addition to those removed from FIG. 17A when both extraction techniques are used. Similarly, 4 more false-positives can be removed using the feature thresholds $C_1$, $C_2$ and $C_3$ illustrated in FIG. 17C.

Using these three feature extraction techniques, it is possible to remove another 18 false-positives. Some of the false-positives removed by the various techniques can overlap. In the case of the techniques and particular data of FIGS. 17A–17C, there were four overlapped false-positives making the actual number of additional false-positives removed fourteen, resulting in removing 79% (44/56) of the false-positives using the third embodiment.

In the third embodiment, one or several feature extraction techniques may be used on the image output by the shift-invariant neural network. The number and particular techniques selected will depend upon desired system parameters. For instance, if very high detection accuracy is desired, then several techniques may be employed. On the other hand, if speed or minimization of system usage is desired, then only one or two techniques could be used.

The system according to the third embodiment is shown in FIG. 18. The system includes an apparatus for obtaining a digital mammogram 90 which outputs a digitized mammogram to a CAD detector 91 and a ROI selector 92. The CAD detector 91 detects suspected microcalcifications which are used by the ROI selector 92 to select ROIs suspected of containing a clustered microcalcification. The suspect ROIs are output to a background-trend corrector 93 for background trend correction, and then output to a pixel normalizer for normalization of the pixels, as described above. The background-trend corrected and normalized ROIs are input to an input data scaler for scaling the ROIs for input into the shift invariant neural network 141. The shift invariant neural network 141 is trained to detect clustered microcalcifications and outputs an ROI to image thresholder 142 for image thresholding, the suspect ROI after being image thresholded is output to a cluster detector 143 for detecting clustered microcalcifications. The detected clustered microcalcification data are input into a second ROI selector 92 which is used to select ROIs from the digital mammogram suspected of having clustered microcalcifications. The microcalcifications are selected using the output image of the shift-invariant neural network 141. The second suspected ROIs are input to an image feature analyzer 180 for performing image feature analysis, as described above. The image features are classified by classifier 181 which performs removal of the false-positive microcalcifications from the suspect ROI. The classifier 181 performs the feature thresholding as described above in relation to FIGS. 16A–16D and 17A–17C. Classifier 181 is typically implemented using software. The output from the classifier 181 is sent to a display device 99 for displaying the suspected clustered microcalcifications on the original digitized mammogram. As pointed out above, using the image feature analyzer 180 and image feature classifier 181 removes additional false-positives resulting in a more accurate system for detecting clustered microcalcifications in a digitized mammogram.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of detecting microcalcifications in a digital mammogram, comprising:

obtaining a digital mammogram;

extracting regions of interest from said digital mammogram suspected of containing a microcalcification;

converting said regions of interest into corresponding numerical data;

inputting said numerical data to a shift-invariant neural network trained to detect microcalcifications for processing of said numerical data by said neural network, said neural network outputting corresponding output images;

detecting a microcalcification in said digital mammogram using said output images.

2. A method as recited in claim 1, wherein extracting regions of interest comprises extracting regions of interest suspected of containing a clustered microcalcification.

3. A method as recited in claim 2, wherein said extracting of regions of interest suspected of containing clustered microcalcifications includes selecting regions of interest containing false-positive microcalcifications; and wherein processing by said neural network includes removing a portion of said false-positive microcalcifications selected in said extracting step.

4. A method as recited in claim 3, wherein extracting a region of interest comprises extracting a region of interest suspected of containing an individual microcalcification.

5. A method as recited in claim 1, wherein processing said region of interest comprises:

background-trend correcting said regions of interest to produce background-trend corrected regions of interest; and converting said background-trend corrected region of interest into numerical data.

6. A method as recited in claim 1, wherein said extracting regions of interest suspected of containing a microcalcification includes selecting regions of interest containing false-positive microcalcifications; and wherein processing by said neural network includes removing a portion of said false-positive microcalcifications selected in said extracting step.

7. A method as recited in claim 1, wherein extracting said regions of interest comprises extracting spatial domain regions of interest.

8. A system for detecting microcalcifications in a digital mammogram, comprising:

a device for obtaining a digital mammogram;

a detector connected to said device which detects suspected microcalcifications in said digital mammogram;

a region of interest selector, connected to said device and said detector, which selects regions of interest in said digital mammogram corresponding to said suspected microcalcifications;

a region of interest processing device outputting processed regions of interest;

an input data scaler connected to said region of interest processing device for numerically scaling said processed regions of interest;

a shift-invariant neural network receiving as input data said numerically scaled regions of interest from said input data scaler and outputting corresponding output images; and a microcalcification detector for detecting microcalcifications in said output images.

9. A system as recited in claim 8, wherein said region of interest extractor comprises a spatial domain region of interest extractor.

10. A method of detecting clustered microcalcifications in a digital mammogram, comprising:

obtaining a digital mammogram;

extracting regions of interest from said digital mammogram suspected of containing a clustered microcalcification;

converting said regions of interest into corresponding numerical data;

inputting said numerical data into a shift-invariant neural network trained to detect clustered microcalcifications;

processing said numerical data by said shift-invariant neural network to produce corresponding output images;

detecting a clustered microcalcification in said digital mammogram using said output images.

11. A method as recited in claim 10, wherein said extracting regions of interest suspected of containing a microcalcification includes selecting regions of interest containing false-positive microcalcifications using a computer-aided diagnostic technique; and wherein processing by said shift-invariant neural network includes removing a portion of said false-positive microcalcifications selected in said extracting step.

12. A method as recited in claim 10, wherein extracting said regions of interest comprises:

detecting suspected clustered microcalcifications in said digital mammogram using a computer-aided diagnostic technique;

selecting regions of interest from said digital mammogram corresponding to said suspected clustered microcalcifications.

13. A method as recited in claim 10, further comprising:

processing said input data using a neural network having an input layer having a plurality of input units, at least one hidden layer having a plurality of groups, each of said groups having a plurality of units, an output layer, and connection weights between said layers; and selecting said connection weights to be shift-invariant as $$w(i,j;x,y)=w(i-x,j-y)$$

where $w(i,j;x,y)$ denotes a connection weight between a unit at a location $(i,j)$ in a first layer and a unit at a location $(x,y)$ in a subsequent layer.

14. A method as recited in claim 13, further comprising:

training said neural network using a modified error back propagation method:

$$\Delta W_{p,q}^l(x, y) = \eta \delta_q^{l+1}(x, y) * O_p^l(x, y) + \alpha W_{p,q}^l(x, y)$$

$$\Delta b_p^l = \eta \sum_i \sum_j \delta_p^l(x, y) + \alpha b_p^l$$

$$\tilde{W}_{p,q}^l(x, y) = W_{p,q}^l(-x, -y)$$

and in the case of said output layer, $$\delta_l^L(x,y)=f'(N_l^L(x,y)+b_l^L)[T(x,y)-O_l^L(x,y)]$$

where:

$N_p^l(x,y)$ is an input of the unit at said location (x,y);

$W_{p,q}^l(x, y)$ is the connection weights;

$O_p^l(x,y)$ is an output of the unit at said location (x,y);

$l=(1,2,\ldots L)$ is a layer number;

$p=(1,2,\ldots P^l)$ is a group number in a lth layer;

$q=(1,2,\ldots P^l+1)$ is a group number in a (l+1)th layer;

$f(x)$ is a thresholding function;

$f'(x)$ is a derivative of $f(x)$;

$\Delta w_{p,q}^l(x,y)$ is a change of the connection weight;

$\Delta b_p^l$ is a change in a bias;

$\eta$ is a learning rate;

$\alpha$ is a the constant factor of a moment term; and $T(x,y)$ is a desired output image.

15. A method as recited in claim 13, further comprising:

each unit in a group receiving input from a predetermined number of units in a preceding layer; and selecting said predetermined number based upon a number of individual microcalcifications in a clustered microcalcification.

16. A method as recited in claim 13, further comprising:

processing said input data using a neural network having one input layer having one of said groups, a first hidden layer having two of said groups, a second hidden layer having one of said groups, and one output layer having one of said groups; and each of said units receiving input from a predetermined number of units in a preceding layer.

17. A method as recited in claim 10, wherein said converting comprises:

correcting a background-trend of said regions of interest to produce corresponding background-trend corrected regions of interest;

normalizing said background-trend corrected regions of interest to produce corresponding normalized regions of interest;

scaling said normalized regions of interest into numerical data.

18. A method as recited in claim 17, wherein said correcting comprises:

fitting a predetermined curve to said regions of interest to produce corresponding estimated background trends; and subtracting said estimated background trends from corresponding of said regions of interest;

and wherein said normalizing comprises:

$$i(x, y) = \frac{i_t(x, y)N^2}{\sum_{x=1}^{N}\sum_{y=1}^{N}|i_t(x, y)|}$$

where:

$i_t(x,y)$ and $i(x,y)$ denote said regions of interest after background-trend correction and after normalization, respectively; and $N^2$ is a number of pixels in said regions of interest.

19. A method as recited in claim 10, further comprising:

said shift-invariant neural network outputting said output images having areas corresponding to detected microcalcifications;

counting said areas for each of said output images;

determining a region of interest to be a positive region of interest if a number of areas is at least a predetermined value.

20. A method as recited in claim 19, further comprising:

determining a region of interest to be a positive region of interest if said number of areas is at least two.

21. A method as recited in claim 10, wherein said detecting comprises:

image thresholding said output images to yield an output image at a predetermined threshold level of an output image intensity value; and detecting microcalcifications using said image thresholded output images.

22. A method as recited in claim 10, further comprising:

performing image feature analysis on said regions of interest suspected of containing a clustered microcalcification.

23. A method as recited in claim 10, further comprising:

selecting second regions of interest in said digital mammogram corresponding to said clustered microcalcifications detected in said output images;

extracting image features from said second regions of interest;

performing image feature analysis on said extracted image features to identify clustered microcalcifications.

24. A method as recited in claim 23, wherein performing image feature analysis comprises feature thresholding.

25. A method as recited in claim 23, further comprising:

comparing clustered microcalcifications detected by both said shift-invariant neural network and said image feature analysis with true clustered microcalcifications; and removing false-positive microcalcifications from said second regions of interest using said image feature analysis.

26. A method as recited in claim 26, wherein removing said false-positives comprises:

feature thresholding said image feature analysis.

27. A method as recited in claim 26, wherein feature thresholding comprises performing at least one of:

determining a contrast of said detected microcalcification;

determining a size of said detected microcalcification;

determining a first moment of a power spectrum of said second regions of interest;

determining edge gradients in said second regions of interest;

determining cumulative edge gradients in said second regions of interest;

determining an average of an edge-gradient-orientation histogram of said second regions of interest;

determining a standard deviation of an edge-gradient-orientation histogram of said second regions of interest; and determining an average optical density of said second regions of interest.

28. A method as recited in claim 10, wherein extracting said regions of interest comprises extracting spatial domain regions of interest.

29. A system for detecting clustered microcalcifications in a digital mammogram, comprising:

a device for obtaining a digital mammogram;

a detector connected to said device which detects suspected microcalcifications in said digital mammogram;

a region of interest selector, connected to said device and said detector, which selects regions of interest in said digital mammogram corresponding to said suspected microcalcifications;

a region of interest processing device outputting processed regions of interest;

an input data scaler connected to said region of interest processing device for numerically scaling said processed regions of interest;

a shift-invariant neural network trained to detect clustered microcalcifications receiving as input data said numerically scaled regions of interest from said data scaler and outputting corresponding output images; and a microcalcification detector for detecting microcalcifications in said output images.

30. A system as recited in claim 29, wherein said region of interest processing device comprises:

a background-trend corrector for correcting background-trends of said regions of interest; and a pixel value normalizer for normalizing pixels of said background-trend corrected regions of interest.

31. A system as recited in claim 29, further comprising:

an image thresholder for image thresholding said output images.

32. A system as recited in claim 29, wherein said cluster detector comprises:

means for counting a number of clustered microcalcifications in said output image;

means for determining an output image to be positive if said number of clustered microcalcifications is at least a predetermined value.

33. A system as recited in claim 32, wherein said predetermined number is two.

34. A system as recited in claim 29, wherein said neural network comprises:

an input layer having a number of input units determined by a number of pixels in one half of power spectra of said regions of interest;

at least one hidden layer, wherein a number of hidden layers is determined using receiver operating characteristic analysis; and an output layer.

35. A system as recited in claim 29, further comprising:

said neural network having an input layer having a plurality of input units, at least one hidden layer having a plurality of groups, each of said groups having a plurality of units, an output layer, and connection weights between said layers; and connection weights between said layers being shift-invariant as $$w(i,j;x,y)=w(i-x, j-y)$$

where w(i,j;x,y) denotes a connection weight between a unit at a location (i,j) in a first layer and a unit at a location (x,y) in a subsequent layer.

36. A system as recited in claim 29, further comprising:
means for training said neural network using a modified error back propagation method:

$$\Delta W_{p,q}^l(x, y) = \eta \delta_q^{l+1}(x, y) * O_p^l(x, y) + \alpha W_{p,q}^l(x, y)$$

$$\Delta b_p^l = \eta \sum_i \sum_j \delta_p^l(x, y) + \alpha b_p^l$$

$$\tilde{W}_{p,q}^l(x, y) = W_{p,q}^l(-x, -y)$$

and in the case of said output layer, $$\delta_l^L(x,y) = f'(N_l^L(x,y) + b_l^L) [T(x,y) - O_l^L(x,y)]$$

where:

$N_p^l(x,y)$ is an input of the unit at said location (x,y);
$W_{p,q}^l(x,y)$ is the connection weights;
$O_p^l(x,y)$ is an output of the unit at said location (x,y);
l=(1,2, ... L) is a layer number;
p=(1,2, ... $P^l$) is a group number in a lth layer;
q=(1,2, ... $P^l$+1) is a group number in a (l+1)th layer;
$f(x)$ is a thresholding function;
$f'(x)$ is a derivative of $f(x)$;
$\Delta w_{p,q}^l(x,y)$ is a change of the connection weight;
$\Delta b_p^l$ is a change in a bias;
$\eta$ is a learning rate;
$\alpha$ is a the constant factor of a moment term; and
T(x,y) is a desired output image.

37. A system for detecting clustered microcalcifications in a digital mammogram, comprising:
a device for obtaining a digital mammogram;
a detector connected to said device which detects suspected microcalcifications in said digital mammogram;
a region of interest selector, connected to said device and said detector, which selects regions of interest in said digital mammogram corresponding to said suspected microcalcifications;
a region of interest processing device outputting a processed regions of interest;
an input data scaler connected to said region of interest processing device for numerically scaling said processed regions of interest;
a shift-invariant neural network trained to detect clustered microcalcifications receiving as input data said numerically scaled regions of interest from said data scaler and outputting corresponding output images;
a microcalcification detector for detecting microcalcifications in said output images; and
an apparatus for performing image feature analysis on microcalcifications detected by said microcalcification detector.

38. A system as recited in claim 37, wherein said region of interest processing device comprises:
a background-trend corrector for correcting background-trends of said regions of interest; and
a pixel value normalizer for normalizing pixels of said background-trend corrected regions of interest.

39. A system as recited in claim 37, further comprising:
an image thresholder for image thresholding said output images.

40. A system as recited in claim 37, wherein said cluster detector comprises:
means for counting a number of clustered microcalcifications in said output image;
means for determining an output image to be positive if said number of clustered microcalcifications is at least a predetermined value.

41. A system as recited in claim 40, wherein said predetermined number is two.

42. A system as recited in claim 37, wherein said neural network comprises:
an input layer having a number of input units determined by a number of pixels in one half of power spectra of said regions of interest;
at least one hidden layer, wherein a number of hidden layers is determined using receiver operating characteristic analysis; and
an output layer.

43. A system as recited in claim 37, further comprising:
said neural network having an input layer having a plurality of input units, at least one hidden layer having a plurality of groups, each of said groups having a plurality of units, an output layer, and connection weights between said layers; and
connection weights between said layers being shift-invariant as $$w(i,j;x,y) = w(i-x, j-y)$$

where w(i,j;x,y) denotes a connection weight between a unit at a location (i,j) in a first layer and a unit at a location (x,y) in a subsequent layer.

44. A system as recited in claim 37, further comprising:
means for training said neural network using a modified error back propagation method:

$$\Delta W_{p,q}^l(x, y) = \eta \delta_q^{l+1}(x, y) * O_p^l(x, y) + \alpha W_{p,q}^l(x, y)$$

$$\Delta b_p^l = \eta \sum_i \sum_j \delta_p^l(x, y) + \alpha b_p^l$$

$$\tilde{W}_{p,q}^l(x, y) = W_{p,q}^l(-x, -y)$$

and in the case of said output layer, $$\delta_l^L(x,y) = f'(N_l^L(x,y) + b_l^L) [T(x,y) - O_l^L(x,y)]$$

where:

$N_p^l(x,y)$ is an input of the unit at said location (x,y);
$W_{p,q}^l(x,y)$ is the connection weights;
$O_p^l(x,y)$ is an output of the unit at said location (x,y);
l=(1,2, ... L) is a layer number;
p=(1,2, ... $P^l$) is a group number in a lth layer;
q=(1,2, ... $P^l$+1) is a group number in a (l+1)th layer;
$f(x)$ is a thresholding function;
$f'(x)$ is a derivative of $f(x)$;
$\Delta w_{p,q}^l(x,y)$ is a change of the connection weight;
$\Delta b_p^l$ is a change in a bias;
$\eta$ is a learning rate;
$\alpha$ is a the constant factor of a moment term; and
T(x,y) is a desired output image.

45. A system as recited in claim 37, wherein said apparatus for performing image feature analysis comprises:

a image feature extracter; and an image feature classifier connected to said image feature extracter.

46. A system as recited in claim 45, wherein said image feature classifier comprises means for performing feature thresholding.

47. A system as recited in claim 37, further comprising:

a second region of interest selector connected to said microcalcification detector for selecting second regions of interest corresponding to said microcalcifications detected by said microcalcification detector;

a image feature extracter for extracting image features of said microcalcifications in said second regions of interest; and an image feature classifier connected to said image feature extracter.

48. A system as recited in claim 47, further comprising:

a display for displaying said digital mammogram; and wherein said image feature classifier further comprises means for indicating said detected microcalcifications on said displayed digital mammogram.

\* \* \* \* \*